US007090843B1

(12) United States Patent
Francisco et al.

(10) Patent No.: US 7,090,843 B1
(45) Date of Patent: Aug. 15, 2006

(54) RECOMBINANT ANTI-CD30 ANTIBODIES AND USES THEREOF

(75) Inventors: Joseph A. Francisco, Edmonds, WA (US); Grant Risdon, Clayton, MO (US); Alan F. Wahl, Mercer Island, WA (US); Clay Siegall, Edmonds, WA (US)

(73) Assignee: Seattle Genetics, Inc., Bothell, WA (US)

( * ) Notice: Subject to any disclaimer, the term of this patent is extended or adjusted under 35 U.S.C. 154(b) by 0 days.

(21) Appl. No.: 09/724,406

(22) Filed: Nov. 28, 2000

(51) Int. Cl.
*A61K 39/395* (2006.01)
(52) U.S. Cl. .............................. 424/138.1; 424/141.1; 424/155.1; 424/134.1; 424/133.1
(58) Field of Classification Search ............. 424/193.1, 424/138.1, 141.1, 155.1, 134.1, 133.1; 435/7.1; 530/387.3; 514/2
See application file for complete search history.

(56) References Cited

U.S. PATENT DOCUMENTS

| 5,165,923 | A | * | 11/1992 | Thorpe et al. | |
|---|---|---|---|---|---|
| 5,677,430 | A | | 10/1997 | Goodwin et al. | |
| 5,789,554 | A | * | 8/1998 | Leung et al. | 435/6 |
| 5,866,372 | A | | 2/1999 | Stein et al. | |
| 6,033,876 | A | | 3/2000 | Lemke et al. | |
| 2003/0186384 | A1 | | 10/2003 | Barth et al. | |
| 2004/0018194 | A1 | | 1/2004 | Francisco et al. | |
| 2005/0123536 | A1 | | 6/2005 | Law et al. | |

FOREIGN PATENT DOCUMENTS

| DE | 19543039 C1 | | 11/1996 |
|---|---|---|---|
| EP | 0 678 523 A | | 10/1995 |
| WO | WO 91/07437 A2 | | 5/1991 |
| WO | WO 96/22384 | * | 7/1996 |
| WO | WO 97/17374 | | 5/1997 |
| WO | WO 01/80880 A2 | | 11/2001 |
| WO | WO 05/001038 A2 | | 1/2005 |

OTHER PUBLICATIONS

Engert, et al., 1999, Seminars in Hematology, 36(3)282-289.*
da Costa, et al., 2000, Cancer Chemother Pharmacol, 46(suppl):S33-S36.*
Barth et al (Jun. 2000, Blood, vol. 95, p. 3909-14).*
Weigert et al (Nature Dec. 21-28, 1978;276:785-90, abstract).*
Falini et al., 1995, Blood, vol. 85, pp. 1-14.*
Tian et al., Cancer Res. Nov. 15, 1995; 55(22): 5335-41.*
Voet et al., (1990, Biochemistry, John Wiley & Sons, p. 1099-1101 only).*
Arndt et al., 1999, "A Bispecific Diabody That Mediates Natural Killer Cell Cytotoxicity Against Xenotransplantated Human Hodgkin's Tumors," Blood 94(8):2562-2568.

Barth et al., 2000, "Ki-4(scFv)-ETA', a new recombinant anti-CD30 immunotoxin with highly specific cytotoxic activity against disseminated Hodgkin tumors in SCID mice," Blood 95:3909-3914.
Bowen et al., 1993, "Functional Effects of CD30 on a Large Granular Lymphoma Cell Line, YT," J. Immunol. 151:5896-5906.
Cerutti et al., 1998, "CD30 Is a CD40-Inducible Molecule that Negatively Regulates CD40-Mediated Immunoglobulin Class Switching in Non-Antigen-Selected Human B Cells," Immunity 9:247-256.
Del Prete et al., 1995, "CD30-mediated Signaling Promotes the Development of Human T Helper Type 2-like T Cells," J. Exp. Med. 182:1655-1661.
Dürkop et al., 1992, "Molecular cloning and expression of a new member of the nerve growth factor receptor family that is characteristic for Hodgkin's disease.," Cell 68:421-427.
Engert et al., 1990, "Evaluation of Ricin A Chain-containing Immunotoxins Directed against the CD30 Antigen as Potential Reagents for the Treatment of Hodgkin's Disease," Cancer Res. 50:84-88.
Engert et al., 1999, "Treatment of Advanced Hodgkin's Lymphoma: Standard and Experimental Approaches," Seminars on Hematology 36(3):282-289.
Falini et al., 1992, "*In vivo* targeting of Hodgkin and Reed-Sternberg cells of Hodgkin's disease with monoclonal antibody Ber-H2 (CD30): immunohistological evidence," British J. Haemat. 82:38-45.
Falini et al., 1992, "Response of refractory Hodgkin's disease to monoclonal anti-CD30 immunotoxin," The Lancet 339:1195-1196.
Franke et al., 2000, "Characterization of the CD30L Binding Domain on the Human CD30 Molecule Using Anti-CD30 Antibodies," Hybridoma 19:43-48.
Grell et al., 1999, "Induction of cell death by tumour necrosis factor (TNF) receptor 2, CD40 and CD30: a role for TNF-R1 activation by endogenous membrane-anchored TNF," EMBO J. 18(11):3034-3043.

(Continued)

*Primary Examiner*—Misook Yu
(74) *Attorney, Agent, or Firm*—Vita G. Conforti; Mark G. Sandbaken; Jones Day

(57) ABSTRACT

The present invention relates to methods and compositions for the treatment of Hodgkin's Disease, comprising administering proteins characterized by their ability to bind to CD30, or compete with monoclonal antibodies AC10 or HeFi-1 for binding to CD30, and exert a cytostatic or cytotoxic effect on Hodgkin's Disease cells. Such proteins include derivatives of monoclonal antibodies AC10 and HeFi-1. The proteins of the invention can be human, humanized, or chimeric antibodies; further, they can be conjugated to cytotoxic agents such as chemotherapeutic drugs. The invention further relates to nucleic acids encoding the proteins of the invention. The invention yet further relates to a method for identifying an anti-CD30 antibody useful for the treatment or prevention of Hodgkin's Disease.

18 Claims, 6 Drawing Sheets

OTHER PUBLICATIONS

Figure 1B:
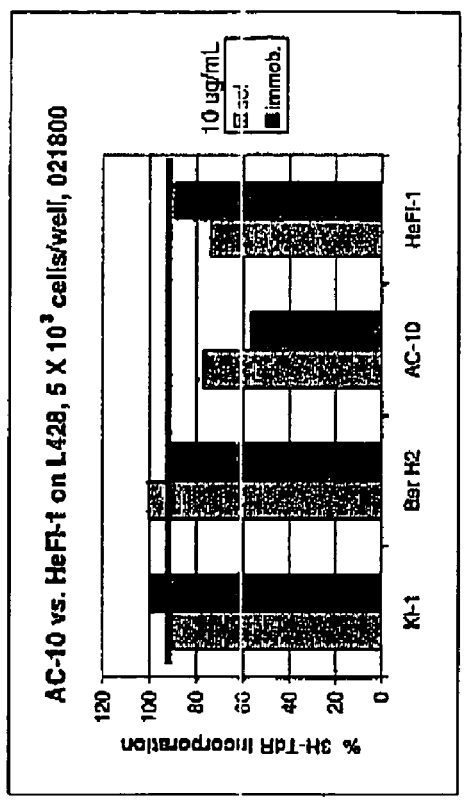

Gruss et al., 1994, "Pleiotrophic Effects of the CD30 Ligand on CD30-Expressing Cells and Lymphoma Cell Lines," Blood 83(8):2045-2056.

Hansen et al., 1991, "Antibody-enhanced shedding of the CD30 (Ki-1) antigen and biochemical analysis of its soluble form," Immunobiol. 183:214.

Hecht et al., 1985, "Production and Characterization of a Monoclonal Antibody That Binds Reed-Sternber Cells," J. Immunol. 134(6):4231-4236.

Horn-Lohrens et al., 1995, "Shedding of the Soluble Form of CD30 From the Hodgkin-Analogose Cell Line L540 is Strongly Inhibited by a new CD30-Specific Antibody (Ki-4)," Int. J. Cancer 60:539-544.

Hsu et al., 1987, "Effect of Monoclonal Antibodies Anti-2H9, Anti-IRac, and Anti-HeFi-1 on the Surface Antigens of Reed-Sternberg Cells," JNCI 79(5):1091-1099.

Hübinger et al., 1999, "The tyrosine kinase NPM-ALK, associated with anaplastic large cell lymphoma, binds the intracellular domain of the suface receptor CD30 but is not activated by CD30 stimulation," Exp. Hematol. 27:1796-1805.

Josimovic-Alasevic et al., 1989, "Ki-1 (CD30) antigen is released by Ki-1-positive tumor cells in vitro and in vivo. I. Partial characterization of soluble Ki-1 antigen and detection of the antigen in cell culture supernatants and in serum by an enzyme-linked immunosorbent assay," Eur. J. Immunol. 19:157-162.

Leca et al., 1994, "A Monoclonal Antibody to the Hodgkin's Disease-Associated Antigen CD30 Induces Activation and Long-Term Growth of Human Autoreactive γδ T Cell Clone," Cell. Immunol. 156:230-239.

Masuda et al., 1998, "Dual action of CD30 antigen: Anti-CD30 antibody induced apoptosis and interleukin-8 secretion in Ki-1 lymphoma cells," Int. J. Hematol. 67:257-265.

May et al., 1990, "Evaluation of ricin A chain-containing immunotoxins directed against different epitopes on the delta-chain of cell surface-associated IgD on murine B cells," J. Immunol. 144:3637-3642.

Mir et al., 2000, "Differential effects of CD30 activation in anaplastic large cell lymphoma and Hodgkin disease cells," Blood 96(13):4307-4312.

Nawrocki et al., "Biochemical and Structural Properties of a Hodgkin's Disease-Related Membrane Protein," J. Immunol. 141:672-680.

Pallesen, 1990, "The diagnostic significance of the CD30 (Ki-1) antigen," Histopatholgoy 16:409-413.

Powell et al., 1998, "Construction and expression of a soluble form of human CD30 ligand with functional activity," J. Leukocyte Biology 63:752-757.

Press et al., 1988, "Ricin A-chain containing immunotoxins directed against different epitopes on the CD2 molecule differ in their ability to kill normal and malignant T cells," J. Immunol. 141:4410-4417.

Renner et al., 2000, "Initiation of humoral and cellular immune responses in patients with refractory Hodgkin's disease by treatment with an anti-CD16/CD30 bispecific antibody," Cancer Immunol. Immunother. 49:173-180.

Schwab et al., 1982, "Production of a monoclonal antibody specific for Hodgkin and Sternberg-Reed cells of Hodgkin's disease and a subset of normal lymphoid cells," Nature 299:65-67.

Schwarting et al., 1989, "BER-H2: a new anti-Ki-1 (CD30) monoclonal antibody directed at a formol-resistant epitope," Blood, Blood 74:1678-1689.

Smith et al., 1993, "CD30 Antigen, a Marker for Hodgkin's Lymphoma, Is a Receptor Whose Ligand Defines an Emerging Family of Cytokines with Homology to TNF," Cell 73:1349-1360.

Tian et al., "*in vivo* Antitiumor Effects of Unconjugated CD30 Monoclonal Antibodies of Human Anaplastic Large-Cell Lymphoma Xenografts," Cancer Res. 55:5335-5341.

Tsutsumi et al., 2000, "Site-specific chemical modification with polyethylene glycol of recombinant immunotoxin anti-Tac(Fv)-PE38 (LMB-2) improves antitumor activity and reduces animal toxicity and immunogenicity," Proc. Natl. Acad. Sci, USA 97:8548-8553.

Tutt et al., 1998, "Monoclonal antibody therapy of B cell lymphoma: signaling activity on tumor cells appears more important than recruitment of effectors," J. Immunol. 161:3176-3185.

Hombach et al., 1998, "Generation of the single chain antibody fragment conserves the idiotypic profile of the anti-CD30 monoclonal antibody HRS3," Scand. J. Immunol. 48(5):497-501.

Schnell et al., 1995, Development of New Ricin A-Chain Immunotoxins with Potent Anti-Tumor Effects Against Human Hodgkin Cells in Vitro and Disseminated Hodgkin Tumors in SCID Mice, (1995).

Bauer al., 1999, "Immunotherapy of Human Tumors with T-Cell-activating Bispecific Antibodies: Stimulation of Cytotoxic Pathways *in Vivo*," Cancer Research, 59:1961-65.

Pohl et al., 1993, "CD30-Antigen-Specific Targeting and Activation of T Cells Via Murine Bispecific Monoclonal Antibodies Against CD3 and CD28: Potential Use for the Treatment of Hodgkin's Lymphoma," Int. J. Cancer 54:820-27.

Renner and Pfreundschuh, 1995, "Tumor Therapy by Immune Recruitment with Bispecific Antobodies," Immunoloy Reviews, 145:178-209.

Pohl et al., "CD30-Specific AB1-AB2-AB3 Internal Image Antibody Network: Potential Use as Anti-Idiotype Vaccine Against Hodgkin's Lymphoma," *Int. J. Cancer* 54:418-425 (1993).

Weigert et al., "Rearrangement of Genetic Information May Produce Immunoglobulin Diversity," *Nature* 276:785-790 (1978).

\* cited by examiner

SEQUENCE LISTING

<160> NUMBER OF SEQ ID NOS: 32

<210> SEQ ID NO 1
<211> LENGTH: 351
<212> TYPE: DNA
<213> ORGANISM: Mus musculus
<220> FEATURE:
<221> NAME/KEY: CDS
<222> LOCATION: (1)...(351)

<400> SEQUENCE: 1

```
cag atc cag ctg cag cag tct gga cct gag gtg gtg aag cct ggg gct      48
Gln Ile Gln Leu Gln Gln Ser Gly Pro Glu Val Val Lys Pro Gly Ala
 1               5                  10                  15 tca gtg aag ata tcc tgc aag gct tct ggc tac acc ttc act gac tac      96
Ser Val Lys Ile Ser Cys Lys Ala Ser Gly Tyr Thr Phe Thr Asp Tyr
             20                  25                  30 tat ata acc tgg gtg aag cag aag cct gga cag gga ctt gag tgg att     144
Tyr Ile Thr Trp Val Lys Gln Lys Pro Gly Gln Gly Leu Glu Trp Ile
         35                  40                  45 gga tgg att tat cct gga agc ggt aat act aag tac aat gag aag ttc     192
Gly Trp Ile Tyr Pro Gly Ser Gly Asn Thr Lys Tyr Asn Glu Lys Phe
     50                  55                  60 aag ggc aag gcc aca ttg act gta gac aca tcc tcc agc aca gcc ttc     240
Lys Gly Lys Ala Thr Leu Thr Val Asp Thr Ser Ser Ser Thr Ala Phe
 65                  70                  75                  80 atg cag ctc agc agc ctg aca tct gag gac act gct gtc tat ttc tgt     288
Met Gln Leu Ser Ser Leu Thr Ser Glu Asp Thr Ala Val Tyr Phe Cys
                 85                  90                  95 gcg aac tat ggt aac tac tgg ttt gct tac tgg ggc caa ggg act cag     336
Ala Asn Tyr Gly Asn Tyr Trp Phe Ala Tyr Trp Gly Gln Gly Thr Gln
            100                 105                 110 gtc act gtc tct gca                                                  351
Val Thr Val Ser Ala
        115
```

<210> SEQ ID NO 2
<211> LENGTH: 117
<212> TYPE: PRT
<213> ORGANISM: Mus musculus

<400> SEQUENCE: 2

```
Gln Ile Gln Leu Gln Gln Ser Gly Pro Glu Val Val Lys Pro Gly Ala
 1               5                  10                  15

Ser Val Lys Ile Ser Cys Lys Ala Ser Gly Tyr Thr Phe Thr Asp Tyr
             20                  25                  30

Tyr Ile Thr Trp Val Lys Gln Lys Pro Gly Gln Gly Leu Glu Trp Ile
         35                  40                  45

Gly Trp Ile Tyr Pro Gly Ser Gly Asn Thr Lys Tyr Asn Glu Lys Phe
     50                  55                  60

Lys Gly Lys Ala Thr Leu Thr Val Asp Thr Ser Ser Ser Thr Ala Phe
 65                  70                  75                  80

Met Gln Leu Ser Ser Leu Thr Ser Glu Asp Thr Ala Val Tyr Phe Cys
                 85                  90                  95

Ala Asn Tyr Gly Asn Tyr Trp Phe Ala Tyr Trp Gly Gln Gly Thr Gln
            100                 105                 110

Val Thr Val Ser Ala
        115
```

```
<210> SEQ ID NO 3
<211> LENGTH: 15
<212> TYPE: DNA
<213> ORGANISM: Mus musculus

<400> SEQUENCE: 3
gactactata taacc                                                    15

<210> SEQ ID NO 4
<211> LENGTH: 5
<212> TYPE: PRT
<213> ORGANISM: Mus musculus

<400> SEQUENCE: 4

Asp Tyr Tyr Ile Thr
 1               5

<210> SEQ ID NO 5
<211> LENGTH: 51
<212> TYPE: DNA
<213> ORGANISM: Mus musculus

<400> SEQUENCE: 5
tggatttatc ctggaagcgg taatactaag tacaatgaga agttcaaggg c             51

<210> SEQ ID NO 6
<211> LENGTH: 17
<212> TYPE: PRT
<213> ORGANISM: Mus musculus

<400> SEQUENCE: 6

Trp Ile Tyr Pro Gly Ser Gly Asn Thr Lys Tyr Asn Glu Lys Phe Lys
 1               5                  10                  15

Gly

<210> SEQ ID NO 7
<211> LENGTH: 24
<212> TYPE: DNA
<213> ORGANISM: Mus musculus

<400> SEQUENCE: 7
tatggtaact actggtttgc ttac                                          24

<210> SEQ ID NO 8
<211> LENGTH: 8
<212> TYPE: PRT
<213> ORGANISM: Mus musculus

<400> SEQUENCE: 8

Tyr Gly Asn Tyr Trp Phe Ala Tyr
 1               5

<210> SEQ ID NO 9
<211> LENGTH: 333
<212> TYPE: DNA
<213> ORGANISM: Mus musculus
<220> FEATURE:
<221> NAME/KEY: CDS
<222> LOCATION: (1)...(333)

<400> SEQUENCE: 9 gac att gtg ctg acc caa tct cca gct tct ttg gct gtg tct cta ggg    48
Asp Ile Val Leu Thr Gln Ser Pro Ala Ser Leu Ala Val Ser Leu Gly
 1               5                  10                  15
```

```
cag agg gcc acc atc tcc tgc aag gcc agc caa agt gtt gat ttt gat        96
Gln Arg Ala Thr Ile Ser Cys Lys Ala Ser Gln Ser Val Asp Phe Asp
         20                  25                  30 ggt gat agt tat atg aac tgg tac caa cag aaa cca gga cag cca ccc       144
Gly Asp Ser Tyr Met Asn Trp Tyr Gln Gln Lys Pro Gly Gln Pro Pro
     35                  40                  45 aaa gtc ctc atc tat gct gca tcc aat cta gaa tct ggg atc cca gcc       192
Lys Val Leu Ile Tyr Ala Ala Ser Asn Leu Glu Ser Gly Ile Pro Ala
 50                  55                  60 agg ttt agt ggc agt ggg tct ggg aca gac ttc acc ctc aac atc cat       240
Arg Phe Ser Gly Ser Gly Ser Gly Thr Asp Phe Thr Leu Asn Ile His
 65                  70                  75                  80 cct gtg gag gag gag gat gct gca acc tat tac tgt cag caa agt aat       288
Pro Val Glu Glu Glu Asp Ala Ala Thr Tyr Tyr Cys Gln Gln Ser Asn
                 85                  90                  95 gag gat ccg tgg acg ttc ggt gga ggc acc aag ctg gaa atc aaa           333
Glu Asp Pro Trp Thr Phe Gly Gly Gly Thr Lys Leu Glu Ile Lys
             100                 105                 110

<210> SEQ ID NO 10
<211> LENGTH: 111
<212> TYPE: PRT
<213> ORGANISM: Mus musculus

<400> SEQUENCE: 10

Asp Ile Val Leu Thr Gln Ser Pro Ala Ser Leu Ala Val Ser Leu Gly
 1               5                  10                  15

Gln Arg Ala Thr Ile Ser Cys Lys Ala Ser Gln Ser Val Asp Phe Asp
             20                  25                  30

Gly Asp Ser Tyr Met Asn Trp Tyr Gln Gln Lys Pro Gly Gln Pro Pro
         35                  40                  45

Lys Val Leu Ile Tyr Ala Ala Ser Asn Leu Glu Ser Gly Ile Pro Ala
     50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                 85                  90                  95

Glu Asp Pro Trp Thr Phe Gly Gly Gly Thr Lys Leu Glu Ile Lys
             100                 105                 110

<210> SEQ ID NO 11
<211> LENGTH: 45
<212> TYPE: DNA
<213> ORGANISM: Mus musculus

<400> SEQUENCE: 11
aaggccagcc aaagtgttga ttttgatggt gatagttata tgaac                      45

<210> SEQ ID NO 12
<211> LENGTH: 15
<212> TYPE: PRT
<213> ORGANISM: Mus musculus

<400> SEQUENCE: 12

Lys Ala Ser Gln Ser Val Asp Phe Asp Gly Asp Ser Tyr Met Asn
 1               5                  10                  15

<210> SEQ ID NO 13
<211> LENGTH: 21
<212> TYPE: DNA
```

-continued

```
<213> ORGANISM: Mus musculus

<400> SEQUENCE: 13
gctgcatcca atctagaatc t                                              21

<210> SEQ ID NO 14
<211> LENGTH: 7
<212> TYPE: PRT
<213> ORGANISM: Mus musculus

<400> SEQUENCE: 14

Ala Ala Ser Asn Leu Glu Ser
 1               5

<210> SEQ ID NO 15
<211> LENGTH: 27
<212> TYPE: DNA
<213> ORGANISM: Mus musculus

<400> SEQUENCE: 15
cagcaaagta atgaggatcc gtggacg                                        27

<210> SEQ ID NO 16
<211> LENGTH: 9
<212> TYPE: PRT
<213> ORGANISM: Mus musculus

<400> SEQUENCE: 16

Gln Gln Ser Asn Glu Asp Pro Trp Thr
 1               5

<210> SEQ ID NO 17
<211> LENGTH: 375
<212> TYPE: DNA
<213> ORGANISM: Mus musculus
<220> FEATURE:
<221> NAME/KEY: CDS
<222> LOCATION: (1)...(375)

<400> SEQUENCE: 17 gag gtg aag ctg gtg gag tct gga gga ggc ttg gta cag cct ggg ggt     48
Glu Val Lys Leu Val Glu Ser Gly Gly Gly Leu Val Gln Pro Gly Gly
 1               5                  10                  15 tct ctg aga ctc tcc tgt gca act tct ggg ttc acc ttc agt gat tac     96
Ser Leu Arg Leu Ser Cys Ala Thr Ser Gly Phe Thr Phe Ser Asp Tyr
             20                  25                  30 tat atg aac tgg gtc cgc cag cct cca gga aag gct ctt gag tgg ttg    144
Tyr Met Asn Trp Val Arg Gln Pro Pro Gly Lys Ala Leu Glu Trp Leu
         35                  40                  45 ggt ttt att aga aac aaa gct aat ggt tac aca aca gag ttc agt gca    192
Gly Phe Ile Arg Asn Lys Ala Asn Gly Tyr Thr Thr Glu Phe Ser Ala
     50                  55                  60 tct gtg atg ggt cgg ttc acc atc tcc aga gat gat tcc caa agc atc    240
Ser Val Met Gly Arg Phe Thr Ile Ser Arg Asp Asp Ser Gln Ser Ile
 65                  70                  75                  80 ctc tat ctt cag atg aac acc ctg aga gct gag gac agt gcc act tat    288
Leu Tyr Leu Gln Met Asn Thr Leu Arg Ala Glu Asp Ser Ala Thr Tyr
                 85                  90                  95 tac tgt gca aga gat ccc ccc tat ggt aac ccc cat tat tat gct atg    336
Tyr Cys Ala Arg Asp Pro Pro Tyr Gly Asn Pro His Tyr Tyr Ala Met
            100                 105                 110 gac tac tgg ggt caa gga acc tca gtc acc gtc tcc tca                375
Asp Tyr Trp Gly Gln Gly Thr Ser Val Thr Val Ser Ser
```

<210> SEQ ID NO 18
<211> LENGTH: 125
<212> TYPE: PRT
<213> ORGANISM: Mus musculus

<400> SEQUENCE: 18

Glu Val Lys Leu Val Glu Ser Gly Gly Gly Leu Val Gln Pro Gly Gly
1               5                   10                  15
Ser Leu Arg Leu Ser Cys Ala Thr Ser Gly Phe Thr Phe Ser Asp Tyr
            20                  25                  30
Tyr Met Asn Trp Val Arg Gln Pro Pro Gly Lys Ala Leu Glu Trp Leu
        35                  40                  45
Gly Phe Ile Arg Asn Lys Ala Asn Gly Tyr Thr Thr Glu Phe Ser Ala
    50                  55                  60
Ser Val Met Gly Arg Phe Thr Ile Ser Arg Asp Asp Ser Gln Ser Ile
65                  70                  75                  80
Leu Tyr Leu Gln Met Asn Thr Leu Arg Ala Glu Asp Ser Ala Thr Tyr
                85                  90                  95
Tyr Cys Ala Arg Asp Pro Pro Tyr Gly Asn Pro His Tyr Tyr Ala Met
            100                 105                 110
Asp Tyr Trp Gly Gln Gly Thr Ser Val Thr Val Ser Ser
        115                 120                 125

<210> SEQ ID NO 19
<211> LENGTH: 15
<212> TYPE: DNA
<213> ORGANISM: Mus musculus

<400> SEQUENCE: 19
gattactata tgaac                                                    15

<210> SEQ ID NO 20
<211> LENGTH: 5
<212> TYPE: PRT
<213> ORGANISM: Mus musculus

<400> SEQUENCE: 20

Asp Tyr Tyr Met Asn
1               5

<210> SEQ ID NO 21
<211> LENGTH: 57
<212> TYPE: DNA
<213> ORGANISM: Mus musculus

<400> SEQUENCE: 21
tttattagaa acaaagctaa tggttacaca acagagttca gtgcatctgt gatgggt     57

<210> SEQ ID NO 22
<211> LENGTH: 19
<212> TYPE: PRT
<213> ORGANISM: Mus musculus

<400> SEQUENCE: 22

Phe Ile Arg Asn Lys Ala Asn Gly Tyr Thr Thr Glu Phe Ser Ala Ser
1               5                   10                  15
Val Met Gly

<210> SEQ ID NO 23
<211> LENGTH: 42
<212> TYPE: DNA
<213> ORGANISM: Mus musculus

<400> SEQUENCE: 23
gatcccccct atggtaaccc ccattattat gctatggact ac                          42

<210> SEQ ID NO 24
<211> LENGTH: 14
<212> TYPE: PRT
<213> ORGANISM: Mus musculus

<400> SEQUENCE: 24

Asp Pro Pro Tyr Gly Asn Pro His Tyr Tyr Ala Met Asp Tyr
1               5                   10

<210> SEQ ID NO 25
<211> LENGTH: 333
<212> TYPE: DNA
<213> ORGANISM: Mus musculus
<220> FEATURE:
<221> NAME/KEY: CDS
<222> LOCATION: (1)...(333)

<400> SEQUENCE: 25 gac att gtg ctg acc cag tct cct gct tcc tta gct gtt tct ctg ggg        48
Asp Ile Val Leu Thr Gln Ser Pro Ala Ser Leu Ala Val Ser Leu Gly
1               5                   10                  15 cag agg gcc acc atc tca tgc agg gcc agc aaa agt gtc agt gca tct        96
Gln Arg Ala Thr Ile Ser Cys Arg Ala Ser Lys Ser Val Ser Ala Ser
            20                  25                  30 ggc tat aat tat atg cac tgg tac caa cag aaa gca ggg cag cca ccc        144
Gly Tyr Asn Tyr Met His Trp Tyr Gln Gln Lys Ala Gly Gln Pro Pro
        35                  40                  45 aaa ctc ctc atc cat ctt gca tcc aac cta gaa tct ggg gtc cct gcc        192
Lys Leu Leu Ile His Leu Ala Ser Asn Leu Glu Ser Gly Val Pro Ala
    50                  55                  60 agg ttc agt ggc agt ggg tct ggg aca gac ttc acc ctc aac atc cat        240
Arg Phe Ser Gly Ser Gly Ser Gly Thr Asp Phe Thr Leu Asn Ile His
65                  70                  75                  80 cct gtg gag gag gag gat gct tca acc tat tac tgt cag cac agt ggg        288
Pro Val Glu Glu Glu Asp Ala Ser Thr Tyr Tyr Cys Gln His Ser Gly
                85                  90                  95 gag ctt cca ttc acg ttc ggc tcg ggg aca aag ttg gaa ata aaa           333
Glu Leu Pro Phe Thr Phe Gly Ser Gly Thr Lys Leu Glu Ile Lys
            100                 105                 110

<210> SEQ ID NO 26
<211> LENGTH: 111
<212> TYPE: PRT
<213> ORGANISM: Mus musculus

<400> SEQUENCE: 26

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Ala Ser
            20                  25                  30

Gly Tyr Asn Tyr Met His Trp Tyr Gln Gln Lys Ala Gly Gln Pro Pro
        35                  40                  45

Lys Leu Leu Ile His Leu Ala Ser Asn Leu Glu Ser Gly Val Pro Ala
    50                  55                  60

-continued

```
Arg Phe Ser Gly Ser Gly Ser Gly Thr Asp Phe Thr Leu Asn Ile His
65                  70                  75                  80

Pro Val Glu Glu Glu Asp Ala Ser Thr Tyr Tyr Cys Gln His Ser Gly
                85                  90                  95

Glu Leu Pro Phe Thr Phe Gly Ser Gly Thr Lys Leu Glu Ile Lys
            100                 105                 110

<210> SEQ ID NO 27
<211> LENGTH: 45
<212> TYPE: DNA
<213> ORGANISM: Mus musculus

<400> SEQUENCE: 27
agggccagca aaagtgtcag tgcatctggc tataattata tgcac            45

<210> SEQ ID NO 28
<211> LENGTH: 15
<212> TYPE: PRT
<213> ORGANISM: Mus musculus

<400> SEQUENCE: 28

Arg Ala Ser Lys Ser Val Ser Ala Ser Gly Tyr Asn Tyr Met His
1               5                   10                  15

<210> SEQ ID NO 29
<211> LENGTH: 21
<212> TYPE: DNA
<213> ORGANISM: Mus musculus

<400> SEQUENCE: 29
cttgcatcca acctagaatc t                                      21

<210> SEQ ID NO 30
<211> LENGTH: 7
<212> TYPE: PRT
<213> ORGANISM: Mus musculus

<400> SEQUENCE: 30

Leu Ala Ser Asn Leu Glu Ser
1               5

<210> SEQ ID NO 31
<211> LENGTH: 27
<212> TYPE: DNA
<213> ORGANISM: Mus musculus

<400> SEQUENCE: 31
cagcacagtg gggagcttcc attcacg                                27

<210> SEQ ID NO 32
<211> LENGTH: 9
<212> TYPE: PRT
<213> ORGANISM: Mus musculus

<400> SEQUENCE: 32

Gln His Ser Gly Glu Leu Pro Phe Thr
1               5
```

RECOMBINANT ANTI-CD30 ANTIBODIES AND USES THEREOF

1. FIELD OF THE INVENTION

The present invention relates to methods and compositions for the treatment of Hodgkin's Disease, comprising administering a protein that binds to CD30. Such proteins include recombinant/variant forms of monoclonal antibodies AC10 and HeFi-1, and derivatives thereof. This invention relates to a novel class of monoclonal antibodies directed against the CD30 receptor which, in unmodified form, are capable of inhibiting the growth of CD30-expressing Hodgkin's Disease cells.

2. BACKGROUND OF THE INVENTION

Curative chemotherapy regimens for Hodgkin's disease represent one of the major breakthroughs in clinical oncology. Multi-agent chemotherapy regimens have increased the cure rate to more than 80% for these patients Nevertheless, 3% of patients die from treatment-related causes, and for patients who do not respond to standard therapy or relapse after first-line treatment, the only available treatment modality is high-dose chemotherapy in combination with stem cell transplantation. This treatment is associated with an 80% incidence of mortality, significant morbidity and a five-year survival rate of less than 50% (See e.g., Engert, et al., 1999, Seminars in Hematology 36:282–289).

The primary cause for tumor relapse is the development of tumor cell clones resistant to the chemotherapeutic agents. Immunotherapy represents an alterative strategy which can potentially bypass resistance. Monoclonal antibodies for specific targeting of malignant tumor cells has been the focus of a number of immunotherapeutic approaches. For several malignancies, antibody-based therapeutics are now an acknowledged part of the standard therapy. The engineered anti-CD20 antibody Rituxan®, for example, was approved in late 1997 for the treatment of relapsed low-grade NHL.

CD30 is a 120 kilodalton membrane glycoprotein (Froese et al., 1987, J. Immunol. 139: 2081–87) and a member of the TNF-receptor superfamily. This family includes TNF-RI, TNF-RII, CD30, CD40, OX-40 and RANK, among others.

CD30 is a proven marker of malignant cells in Hodgkin's disease (HD) and anaplastic large cell lymphoma (ALCL), a subset of non-Hodgkin's (NHL) lymphomas (Dürkop et al., 1992, Cell 88:421–427). Originally identified on cultured Hodgkin's-Reed Steinberg (H-RS) cells using the monoclonal antibody Ki-1 (Schwab et al., 1982, Nature 299: 65–67), CD30 is highly expressed on the cell surface of all HD lymphomas and the majority of ALCL, yet has very limited expression in normal tissues to small numbers of lymphoid cells in the perifollicular areas (Josimovic-Alasevic et al., 1989, Eur. J. Immunol. 19:157–162). Monoclonal antibodies specific for the CD30 antigen have been explored as vehicles for the delivery of cytostatic drugs, plant toxins and radioisotopes in both preclinical models and clinical studies (Engert et al., 1990, Cancer Research 50:84–88; Barth et al., 2000, Blood 95:3909–3914). In patients with HD, targeting of the CD30 antigen could be achieved with low doses of the anti-CD30 mAb, BerH2 (Falini et al., 1992, British Journal of Haematology 82:38–45). Yet, despite successful in vivo targeting of the malignant tumor cells, none of the patients experienced tumor regression. In a subsequent clinical trial, a toxin (saporin) was chemically conjugated to the antibody BerH2 and all four patients demonstrated rapid and substantial reductions in tumor mass (Falini et al., 1992, Lancet 339: 1195–1196).

These observations underscore the validity of the CD30 receptor as a target antigen. However, all of the patients treated with the mAb-toxin conjugate developed antibodies to the toxin. One of the major limitations of immunotoxins is their inherent immunogenicity that results in the development of antibodies to the toxin molecule and neutralizes their effects (Tsutsumi et al., 2000, Proc. Nat'l Acad. Sci. U.S.A. 97:8545–8553). Additionally, the liver toxicity and vascular leak syndrome associated with immunotoxins potentially limits the ability to deliver curative doses of these agents (Tsutsumi et al., 2000, Proc. Nat'l Acad. Sci. U.S.A. 97:8545–8553).

2.1 CD30 Monoclonal Antibodies

CD30 was originally identified by the monoclonal antibody Ki-1 and initially referred to as the Ki-1 antigen (Schwab et al., 1982, Nature 299:65–67). This mAb was developed against Hodgkin and Reed-Sternberg (H—RS) cells, the malignant cells of Hodgkin's disease (HD). A second mAb, capable of binding a formalin resistant epitope, different from that recognized by Ki-1 was subsequently described (Schwarting et al., 1989 Blood 74:1678–1689). The identification of four additional antibodies resulted in the creation of the CD30 cluster at the Third Leucocyte Typing Workshop in 1986 (McMichael, A., ed., 1987, Leukocyte Typing III (Oxford: Oxford University Press)).

2.2 CD30 Monoclonal Antibody-Based Therapeutics

The utility of CD30 mAbs in the diagnosis and staging of HD led to their evaluation as potential tools for immunotherapy. In patients with HD, specific targeting of the CD30 antigen was achieved with low doses (30–50 mg) of the anti-CD30 mAb BerH2 (Falini et al., 1992, British Journal of Haematology 82:38–45). Despite successful targeting in vivo of the malignant H—RS tumor cells, none of the patients experienced tumor regressions.

Based on these results, it was concluded that efficacy with CD30 mAb targeted immunotherapy could not be achieved with unmodified antibodies (Falini et al., 1992, Lancet 339:1195–1196). In a subsequent clinical trial, treatment of four patients with refractory HD with a toxin, saporin, chemically conjugated to the mAb BerH2 demonstrated rapid and substantial, although transient, reductions in tumor mass (Falini et al., 1992, Lancet 339:1195–1196). In recent years, investigators have worked to refine the approaches for treating CD30-expressing neoplastic cells. Examples include the development of recombinant single chain immunotoxins (Barth et al., 2000, Blood 95:3909–3914), anti-CD16/CD30 bi-specific mAbs (Renner et al., 2000, Cancer Immunol. Immunother. 49:173–180), and the identification of new anti-CD30 mAbs which prevent the release of CD30 molecules from the cell surface (Horn-Lohrens et al., 1995, Int. J. Cancer 60:539–544). This focus has dismissed the potential of anti-CD30 "mAbs with signaling activity in the treatment of Hodgkin's disease.

2.3. Identification of Anti-CD30 Monoclonal Antibodies with Agonist Activity In cloning and characterizing the biologic activity of the human CD30 ligand (CD30L), two mAbs, M44 and M67, were described which mimicked the activity of CD30L induced receptor crosslinking (Gruss et al., 1994, Blood 83:2045–2056). In in vitro assays, these mAbs, in immobilized form, were capable of stimulating the proliferation of activated T-cells and the Hodgkin's disease cell lines of T-cell origin, L540 and HDLM-2. In contrast, these mAbs had little effect on the Hodgkin's cell lines of B-cell origin, L428 and KM-H2 (Gruss et al., 1994, Blood 83:2045–2056). In all of these assays, the binding of the CD30 receptor by the anti-CD30 mAb Ki-1 had little effect.

The proliferative activity of these agonist anti-CD30 mAbs on Hodgkin's cell lines suggested that anti-CD30 mAbs possessing signaling activity would not have any utility in the treatment of HD.

In contrast, the proliferation of cell lines representing CD30-expressing ALCL was strongly inhibited by the presence of immobilized M44 and M67 mAbs. This inhibitory activity against ALCL cell lines was further extended to in vivo animal studies. The survival of SCID mice bearing ALCL tumor xenografts was significantly increased following the administration of the mAb M44. In addition, the anti-CD30 mAb HeFi-1, recognizing a similar epitope as that of M44, also prolonged survival in this animal model (Tian et al., 1995, Cancer Research 55:5335–5341).

There is a need in the art for therapeutics with increased efficacy to treat or prevent Hodgkin's Disease, a need provided by the present invention. Clinical trials and numerous pre-clinical evaluations have failed to demonstrate antitumor activity of a number of anti-CD30 mAbs in unmodified form against cells representative of Hodgkin's disease. Under conditions similar to those utilized by Gruss et al. in their evaluations of mAbs Ki-1, M44 and M67 (Gruss et al., 1994, Blood 83:2045–2056), we demonstrate a class of CD30 mAbs which is functionally distinct from those previously described. This class of anti-CD30 mAbs is capable of inhibiting the in vitro growth of all Hodgkin's lines tested. Furthermore, these unmodified mAbs possess in vivo antitumor activity against HD tumor xenografts.

2.3.1 Monoclonal Antibody AC10

The majority of murine anti-CD30 mAbs known in the art have been generated by immunization of mice with HD cell lines or purified CD30 antigen. AC10, originally termed C10 (Bowen et al., 1993, J. Immunol. 151:5896–5906), is distinct in that this anti-CD30 mAb that was prepared against a human NK-like cell line, YT (Bowen et al., 1993, J. Immunol. 151:5896–5906). Initially, the signaling activity of this mAb was evidenced by the down regulation of the cell surface expression of CD28 and CD45 molecules, the up regulation of cell surface CD25 expression and the induction of homotypic adhesion following binding of C10 to YT cells.

2.3.2 Monoclonal Antibody HeFi-1

HeFi-1 is an anti-CD30 mAb which was produced by immunizing mice with the L428 Hodgkin's disease cell line (Hecht et al., 1985, J. Immunol. 134:4231–4236). Co-culture of HeFi-1 with the Hodgkin's disease cell lines L428 or L540 failed to reveal any direct effect of the mAb on the viability of these cell lines. In vitro and in vivo antitumor activity of HeFi-1 was described by Tian et al against the Karpas 299 ALCL cell line (Tian et al., 1995, Cancer Research 55:5335–5341).

2.4 Direct Anti-Tumor Activity of Signaling CD30 Antibodies

Monoclonal antibodies represent an attractive approach to targeting specific populations of cells in vivo. Native mAbs and their derivatives may eliminate tumor cells by a number of mechanisms including, but not limited to, complement activation, antibody dependent cellular cytotoxicity (ADCC), inhibition of cell cycle progression and induction of apoptosis (Tutt et al., 1998, J. Immunol. 161:3176–3185).

As described above, mAbs to the CD30 antigen such as Ki-1 and Ber-H2 failed to demonstrate direct antitumor activity (Falini et al., 1992, British Journal of Haematology 82:38–45; Gruss et al., 1994, Blood 83:2045–2056). While some signaling mAbs to CD30, including M44, M67 and HeFi-1, have been shown to inhibit the growth of ALCL lines in vitro (Gruss et al., 1994, Blood 83:2045–2056) or in vivo (Tian et al., 1995, Cancer Res. 55:5335–5341), known anti-CD30 antibodies have not been shown to be effective in inhibiting the proliferation of HD cells in culture. In fact, two signaling anti-CD30 mAbs, M44 and M67, which inhibited the growth of the ALCL line Karpas-299, were shown to enhance the proliferation of T-cell-like HD lines in vitro while showing no effect on B-cell-like HD lines (Gruss et al., 1994, Blood 83:2045–2056).

The conjugate of antibody Ki-1 with the Ricin A-chain made for a rather ineffective immunotoxin and it was concluded that this ineffectiveness was due to the rather low affinity of antibody Ki-1 (Engert et al., 1990, Cancer Research 50:84–88). Two other reasons may also account for the weak toxicity of Ki-1-Ricin A-chain conjugates: a) Antibody Ki-1 enhanced the release of the sCD30 from the Hodgkin-derived cell lines L428 and L540 as well as from the CD30+non-Hodgkin's lymphoma cell line Karpas 299 (Hansen et al., 1991, Immunobiol. 183:214); b) the relatively great distance of the Ki-1 epitope from the cell membrane is also not favorable for the construction of potent immunotoxins (Press et al., 1988, J. Immunol. 141: 4410–4417; May et al., 1990, J. Immunol. 144:3637–3642).

At the Fourth Workshop on Leukocyte Differentiation Antigens in Vienna in February 1989, monoclonal antibodies were submitted by three different laboratories and finally characterized as belonging to the CD30 group. Co-cultivation experiments by the inventors of L540 cells with various antibodies according to the state of the art, followed by the isolation of sCD30 from culture supernatant fluids, revealed that the release of the sCD30 was most strongly increased by antibody Ki-1, and weakly enhanced by the antibody HeFi-1, whilst being more strongly inhibited by the antibody Ber-H2. However, the antibody Ber-H2 also labels a subpopulation of plasma cells (Schwarting et al., 1988, Blood 74:1678–1689) and G. Pallesen (G. Pallesen, 1990, Histopathology 16:409–413) describes, on page 411, that Ber-H2 is cross-reacting with an epitope of an unrelated antigen which is altered by formaldehyde.

Citation or identification of any reference herein shall not be construed as an admission that such reference is available as prior art to the present invention.

3. SUMMARY OF THE INVENTION

The present invention is based on the surprising discovery of a novel activity associated with a certain class of anti-CD30 antibodies, said class comprising AC10 and HeFi-1, namely their ability to inhibit the growth of both T-cell-like and B-cell-like Hodgkin's Disease (HD) cells.

The invention provides proteins that compete for binding to CD30 with monoclonal antibody AC10 or HeFi-1, and exert a cytostatic or cytotoxic effect on a Hodgkin's Disease cell line. The invention further provides antibodies that immunospecifically bind CD30 and exert a cytostatic or cytotoxic effect on a Hodgkin's Disease cell line.

The invention further provides a method for the treatment or prevention of Hodgkin's Disease in a subject comprising administering to the subject, in an amount effective for said treatment or prevention, an antibody that immunospecifically binds CD30 and exerts a cytostatic or cytotoxic effect on a Hodgkin's Disease cell line; and a pharmaceutically acceptable carrier. The invention provides a method for the treatment or prevention of Hodgkin's Disease in a subject comprising administering to the subject an amount of a protein, which protein competes for binding to CD30 with monoclonal antibody AC10 or HeFi-1, and exerts a cytostatic or cytotoxic effect on a Hodgkin's Disease cell line, which amount is effective for the treatment or prevention of Hodgkin's Disease. In one embodiment, a protein of the invention is conjugated to a cytotoxic molecule. In another embodiment, a protein of the invention is a fusion protein comprising the amino acid sequence of a second protein such as bryodin or a pro-drug converting enzyme. The proteins of the invention, including conjugates and fusion proteins, can be used in conjunction with radiation therapy, chemotherapy, hormonal therapy and/or immunotherapy.

In determining the cytostatic effect of the proteins of the invention on Hodgkin's Disease cell lines, a culture of the Hodgkin's Disease cell line is contacted with the protein, said culture being of about 5,000 cells in a culture area of about 0.33 cm$^2$, said contacting being for a period of 72 hours; exposed to 0.5 µCi of $^3$H-thymidine during the final 8 hours of said 72-hour period; and the incorporation of $^3$H-thymidine into cells of the culture, is measured. The protein has a cytostatic or cytotoxic effect on the Hodgkin's Disease cell line if the cells of the culture have reduced $^3$H-thymidine incorporation compared to cells of the same Hodgkin's Disease cell line cultured under the same conditions but not contacted with the protein. Suitable Hodgkin's Disease cell lines to determine the cytostatic or cytotoxic effects of the proteins of the invention are L428, L450, HDLM2 or KM-H2.

Wherein the protein of the invention is an antibody, the antibody is a monoclonal antibody, preferably a recombinant antibody, and most preferably is human, humanized, or chimeric.

The invention further provides isolated nucleic acids encoding a protein that competes for binding to CD30 with monoclonal antibody AC10 or HeFi-1, and exerts a cytostatic or cytotoxic effect on a Hodgkin's Disease cell line. The invention further provides methods of isolating nucleic acids encoding antibodies that immunospecifically bind CD30 and exert a cytostatic or cytotoxic effect on a Hodgkin's Disease cell line.

The invention further provides a method of producing a protein comprising growing a cell containing a recombinant nucleotide sequence encoding a protein, which protein competes for binding to CD30 with monoclonal antibody AC10 or HeFi-1 and exerts a cytostatic or cytotoxic effect on a Hodgkin's Disease cell line, such that the protein is expressed by the cell; and recovering the expressed protein.

The invention yet further provides a method for identifying an anti-CD30 antibody useful for the treatment or prevention of Hodgkin's Disease, comprising determining whether the anti-CD30 antibody exerts a cytostatic or cytotoxic effect on a Hodgkin's Disease cell line by contacting a culture of the Hodgkin's Disease cell line with the protein, said culture being of about 5,000 cells in a culture area of about 0.33 cm$^2$, said contacting being for a period of 72 hours; exposing the culture to 0.5 µCi of $^3$H-thymidine during the final 8 hours of said 72-hour period; and measuring the incorporation of $^3$H-thymidine into cells of the culture. The anti-CD30 antibody has a cytostatic or cytotoxic effect on the Hodgkin's Disease cell line and is useful for the treatment or prevention of Hodgkin's Disease if the cells of the culture have reduced $^3$H-thymidine incorporation compared to cells of the same Hodgkin's Disease cell line cultured under the same conditions but not contacted with the anti-CD30 antibody.

4. BRIEF DESCRIPTION OF THE FIGURES

Figure 1A:
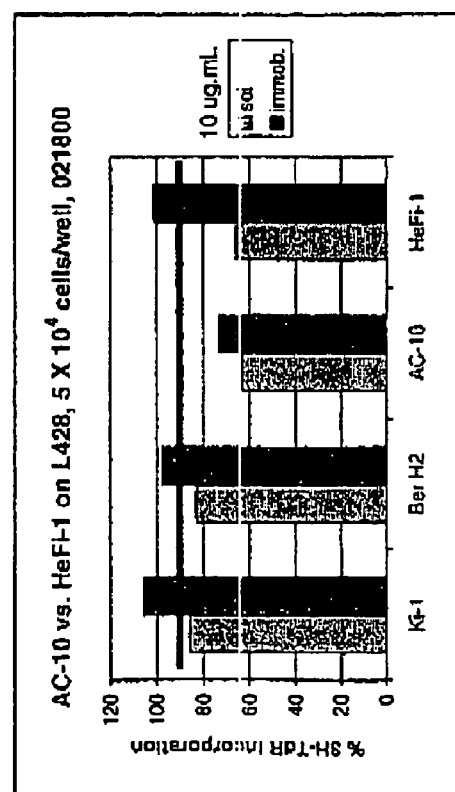

FIG. 1. Growth inhibition of Hodgkin's disease cell lines: Hodgkin's disease cell lines HDLM-2, L540, L428 and KM-H2 were cultured at 5×10$^4$ cells/well in the presence or absence of 10 µg/ml of immobilized AC10. Ki-1 was used as a control in these assays. Proliferation was measured by $^3$H-thymidine incorporation following 72 hours of culture.

Figure 2B:
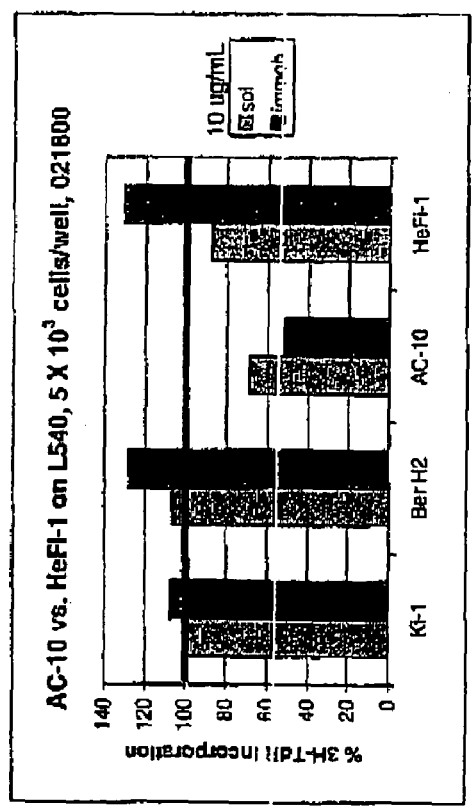
Figure 2A:
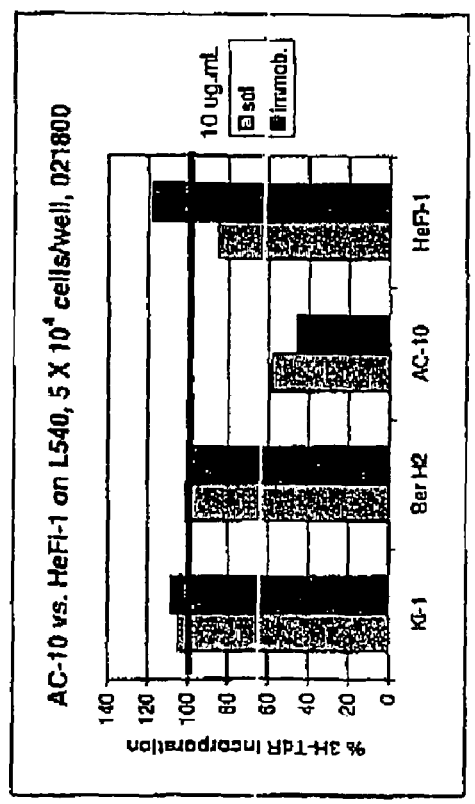

FIG. 2. Growth inhibition of Hodgkin's disease cell lines: Hodgkin's disease cell lines HDLM-2, L540, L428 and KM-H2 were cultured at 5×10$^3$ cells/well in the presence or absence of 10 µg/ml of immobilized AC10. Ki-1 was used as a control in these assays. Proliferation was measured by $^3$H-thymidine incorporation following 72 hours of culture.

Figure 3:
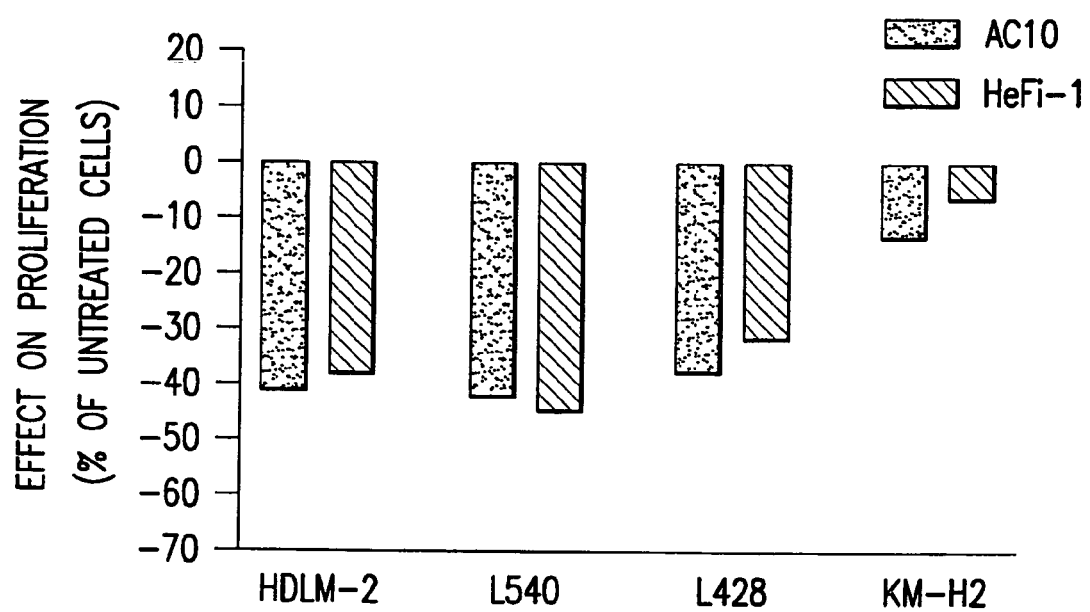

FIG. 3. Growth inhibition of Hodgkin's disease cell lines: Hodgkin's disease cell lines HDLM-2, L540, L428 and KM-H2 were cultured at 5×10$^4$ cells/well in the presence or absence of 0.1 µg/ml AC10 or HeFi-1 that had been cross-linked by the addition of 20 µg/ml polyclonal goat anti-mouse IgG antibodies. Proliferation was measured by $^3$H-thymidine incorporation following 72 hours of culture.

Figure 4:
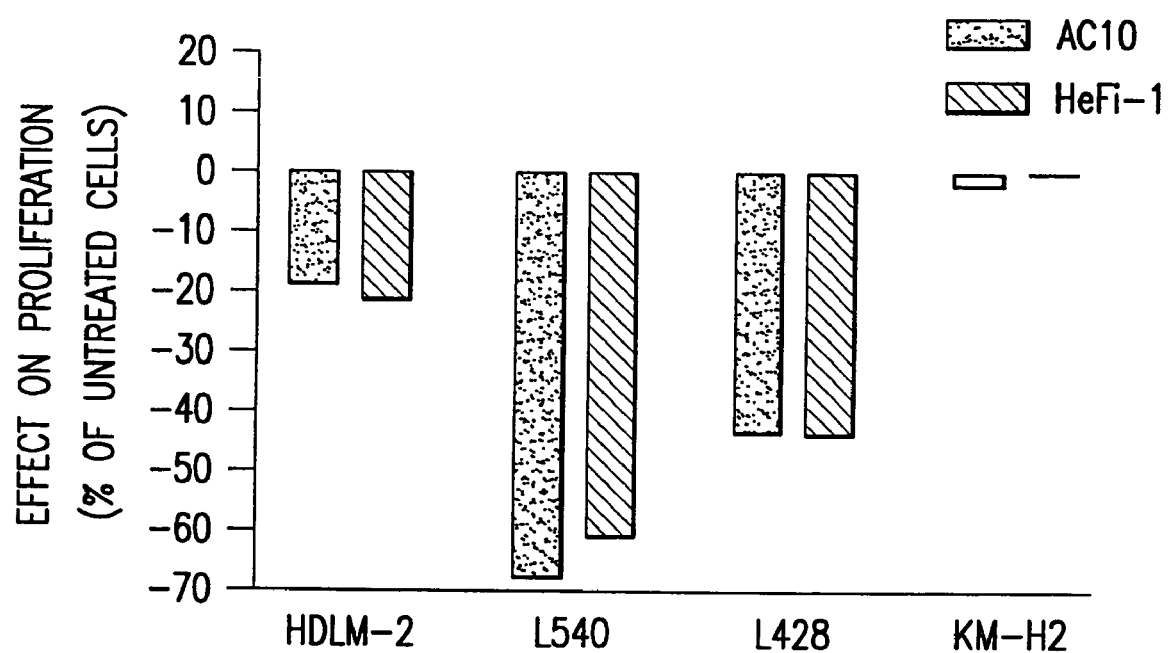

FIG. 4. Growth inhibition of Hodgkin's disease cell lines: Hodgkin's disease cell lines HDLM-2, L540, L428 and KM-H2 were cultured at 5×10$^3$ cells/well in the presence or absence of 0.11 g/ml AC10 or HeFi-1 that had been cross-linked by the addition of 20 µg/ml polyclonal goat anti-mouse IgG antibodies. Proliferation was measured by $^3$H-thymidine incorporation following 72 hours of culture.

FIG. 5. Antitumor activity of AC10 (circles) and HeFi-1 (squares) in disseminated (A) and subcutaneous (B) L540cy Hodgkin's disease xenografts. A) Mice were implanted with 1×10$^7$ cells through the tail vein on day 0 and received intraperitoneal injections of antibody at 1 mg/kg/injection using an administration schedule of q2d×10. B) Mice were implanted subcutaneously with 2×10$^7$ L540cy cells. When tumors were palpable mice were treated with intraperitoneal injections of AC10 or HeFi-1 at 2 mg/kg/injection q2d×10. In both experiments untreated mice (X) received no therapy.

Figure 6:
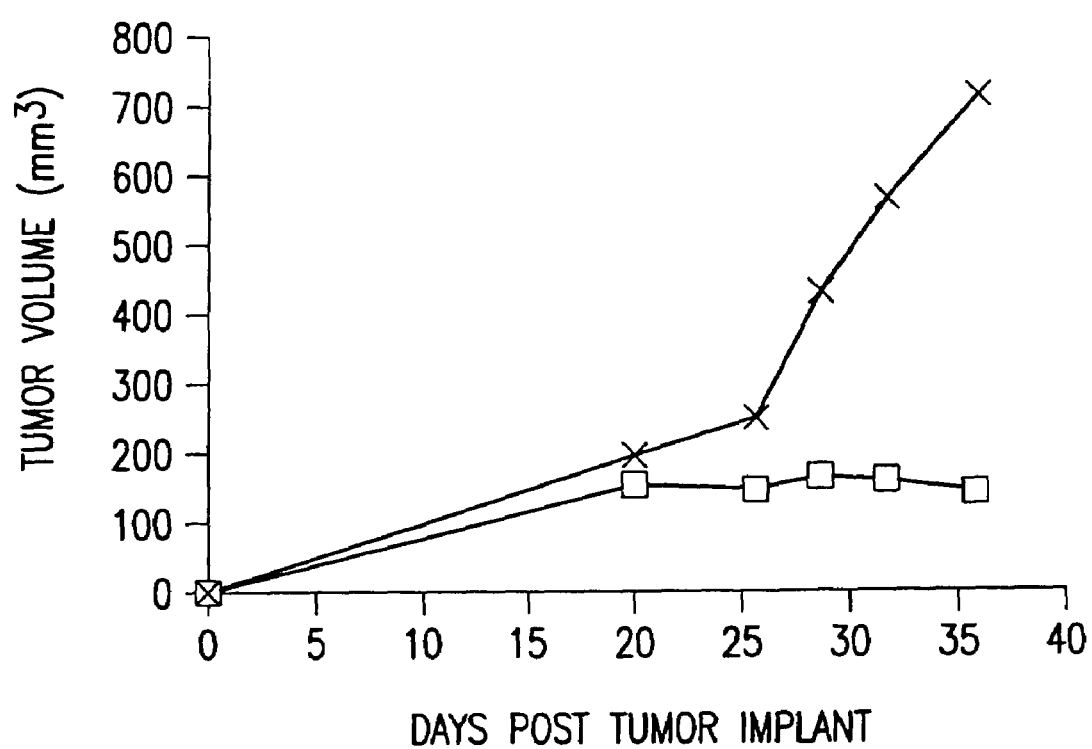

FIG. 6. Antitumor activity of chimeric AC10 (cAC10) in subcutaneous L540cy Hodgkin's disease xenografts. SCID mice were implanted subcutaneously with L540cy cells and when the tumors reached an average size of >150 mm$^3$ mice were either left untreated (X) or treated with cAC10 (□) at 2 mg/kg twice per week for 5 injections.

5. DETAILED DESCRIPTION OF THE INVENTION

The present invention relates to proteins that bind to CD30 and exert a cytostatic or cytotoxic effect on HD cells. The invention further relates to proteins that compete with AC10 or HeFi-1 for binding to CD30 and exert a cytostatic or cytotoxic effect on HD cells. In one embodiment, the protein is an antibody. In a preferred mode of the embodiment, the antibody is AC10 or HeFi-1, most preferably a humanized or chimeric AC10 or HeFi-1.

The invention further relates to proteins encoded by and nucleotide sequences of AC10 and HeFi-1 genes. The invention further relates to fragments and other derivatives and analogs of such AC10 and HeFi-1 proteins. Nucleic acids encoding such fragments or derivatives are also within the scope of the invention. Production of the foregoing proteins, e.g., by recombinant methods, is provided.

The invention also relates to AC10 and HeFi-1 proteins and derivatives including fusion/chimeric proteins which are functionally active, i.e., which are capable of displaying binding to CD30 and exerting a cytostatic or cytotoxic effect on HD cells.

Antibodies to CD30 encompassed by the invention include human, chimeric or humanized antibodies, and such antibodies conjugated to cytotoxic agents such chemotherapeutic drugs.

The invention further relates to methods of treating or preventing HD comprising administering a composition comprising a protein or nucleic acid of the invention alone or in combination with a cytotoxic agent, including but not limited to a chemotherapeutic drug.

For clarity of disclosure, and not by way of limitation, the detailed description of the invention is divided into the subsections which follow.

5.1 Proteins of the Invention

The present invention encompasses proteins, including but not limited to antibodies, that bind to CD30 and exert cytostatic and/or cytotoxic effects on HD cells. The invention further relates to proteins that compete with AC10 or HeFi-1 for binding to CD30 and exert a cytostatic or cytotoxic effect on HD cells.

An ATCC deposit has been made on Apr. 26, 2005 pursuant to the terms of the Budapest Treaty on the international recognition of the deposit of microorganisms for purposes of patent procedure. The ATCC is located at 10801 University Boulevard, Manassas, Va. 20110-2209, USA. The ATCC deposit of the hybridoma: mAC10 was given an accession number of PTA-6679. Any deposit is provided as a convenience to those of skill in the art and is not an admission that a deposit is required under 35 U.S.C. Section 112. That described herein is not to be limited in scope by the antibody deposited, since the deposited embodiment is intended as a single illustration of certain aspects of the invention and any antibody that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

The present invention further encompasses proteins comprising, or alternatively consisting of, a CDR of HeFi-1 (SEQ ID NO:20, SEQ ID NO:22; SEQ ID NO:24; SEQ ID NO:28, SEQ ID NO:30 or SEQ ID NO:32) or AC10 (SEQ ID NO:4; SEQ ID NO:6; SEQ ID NO:8; SEQ ID NO:12; SEQ ID NO:14; or SEQ ID NO:16).

The present invention further encompasses proteins comprising, or alternatively consisting of, a variable region of HeFi-1 (SEQ ID NO:18 or SEQ ID NO:26) or AC10 (SEQ ID NO:2 or SEQ ID NO:10). A table indicating the region of AC10 or HeFi-1 to which each SEQ ID NO corresponds to is provided below:

TABLE 1

| MOLECULE | NUCLEOTIDE OR AMINO ACID | SEQ ID NO |
|---|---|---|
| AC10 Heavy Chain Variable Region | Nucleotide | 1 |
| AC10 Heavy Chain Variable Region | Amino Acid | 2 |
| AC10 Heavy Chain-CDR1 (H1) | Nucleotide | 3 |
| AC10 Heavy Chain-CDR1 (H1) | Amino Acid | 4 |
| AC10 Heavy Chain-CDR2 (H2) | Nucleotide | 5 |
| AC10 Heavy Chain-CDR2 (H2) | Amino Acid | 6 |
| AC10 Heavy Chain-CDR3 (H3) | Nucleotide | 7 |
| AC10 Heavy Chain-CDR3 (H3) | Amino Acid | 8 |
| AC10 Light Chain Variable Region | Nucleotide | 9 |
| AC10 Light Chain Variable Region | Amino Acid | 10 |
| AC10 Light Chain-CDR1 (L1) | Nucleotide | 11 |
| AC10 Light Chain-CDR1 (L1) | Amino Acid | 12 |
| AC10 Light Chain-CDR2 (L2) | Nucleotide | 13 |
| AC10 Light Chain-CDR2 (L2) | Amino Acid | 14 |
| AC10 Light Chain-CDR3 (L3) | Nucleotide | 15 |
| AC10 Light Chain-CDR3 (L3) | Amino Acid | 16 |
| HeFi-1 Heavy Chain Variable Region | Nucleotide | 17 |
| HeFi-1 Heavy Chain Variable Region | Amino Acid | 18 |
| HeFi-1 Heavy Chain-CDR1 (H1) | Nucleotide | 19 |
| HeFi-1 Heavy Chain-CDR1 (H1) | Amino Acid | 20 |
| HeFi-1 Heavy Chain-CDR2 (H2) | Nucleotide | 21 |
| HeFi-1 Heavy Chain-CDR2 (H2) | Amino Acid | 22 |
| HeFi-1 Heavy Chain-CDR3 (H3) | Nucleotide | 23 |
| HeFi-1 Heavy Chain-CDR3 (H3) | Amino Acid | 24 |
| HeFi-1 Light Chain Variable Region | Nucleotide | 25 |
| HeFi-1 Light Chain Variable Region | Amino Acid | 26 |
| HeFi-1 Light Chain-CDR1 (L1) | Nucleotide | 27 |
| HeFi-1 Light Chain-CDR1 (L1) | Amino Acid | 28 |
| HeFi-1 Light Chain-CDR2 (L2) | Nucleotide | 29 |
| HeFi-1 Light Chain-CDR2 (L2) | Amino Acid | 30 |
| HeFi-1 Light Chain-CDR3 (L3) | Nucleotide | 31 |
| HeFi-1 Light Chain-CDR3 (L3) | Amino Acid | 32 |

The present invention further comprises functional derivatives or analogs of AC10 and HeFi-1. As used herein, the term "functional" in the context of a peptide or protein of the invention indicates that the peptide or protein is 1) capable of binding to CD30 and 2) exerts a cytostatic and/or cytotoxic effect on HD cells.

Generally, antibodies of the invention immunospecifically bind CD30 and exert cytostatic and cytotoxic effects on malignant cells in HD. Antibodies of the invention are preferably monoclonal, and may be multispecific, human, humanized or chimeric antibodies, single chain antibodies, Fab fragments, F(ab') fragments, fragments produced by a Fab expression library, and CD30 binding fragments of any of the above. The term "antibody," as used herein, refers to immunoglobulin molecules and immunologically active portions of immunoglobulin molecules, i.e., molecules that contain an antigen binding site that immunospecifically binds CD30. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

In certain embodiments of the invention, the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, CH1, CH2, CH3 and CL domains. Also included in the invention are antigen-binding fragments also comprising any combination of variable region(s) with a hinge region, CH1, CH2, CH3 and CL domains. Preferably, the antibodies are human, murine (e.g., mouse and rat), donkey, sheep, rabbit, goat, guinea pig, camelid, horse, or chicken. As used herein, "human" antibodies include antibodies having the amino acid sequence of a human immunoglobulin and include antibodies isolated from human immunoglobulin libraries, from human B cells, or from animals transgenic for one or more human immunoglobulin, as described infra and, for example in U.S. Pat. No. 5,939,598 by Kucherlapati et al.

The antibodies of the present invention may be monospecific, bispecific, trispecific or of greater multi specificity. Multispecific antibodies may be specific for different epitopes of CD30 or may be specific for both CD30 as well as for a heterologous protein. See, e.g., PCT publications WO 93/17715; WO 92/08802; WO 91/00360; WO 92/05793; Tutt, et al., 1991, J. Immunol. 147:60–69; U.S. Pat. Nos. 4,474,893; 4,714,681; 4,925,648; 5,573,920; 5,601,819; Kostelny et al., 1992, J. Immunol. 148:1547–1553.

Antibodies of the present invention may be described or specified in terms of the particular CDRs they comprise. In certain embodiments antibodies of the invention comprise one or more CDRs of AC10 and/or HeFi-1. The invention encompasses an antibody or derivative thereof comprising a heavy or light chain variable domain, said variable domain comprising (a) a set of three CDRs, in which said set of CDRs are from monoclonal antibody AC10 or HeFi-1, and (b) a set of four framework regions, in which said set of framework regions differs from the set of framework regions in monoclonal antibody AC 10 or HeFi-1, respectively, and in which said antibody or derivative thereof immunospecifically binds CD30.

In a specific embodiment, the invention encompasses an antibody or derivative thereof comprising a heavy chain variable domain, said variable domain comprising (a) a set of three CDRs, in which said set of CDRs comprises SEQ ID NO:4, 6, or 8 and (b) a set of four framework regions, in which said set of framework regions differs from the set of framework regions in monoclonal antibody AC10, and in which said antibody or derivative thereof immunospecifically binds CD30.

In a specific embodiment, the invention encompasses an antibody or derivative thereof comprising a heavy chain variable domain, said variable domain comprising (a) a set of three CDRs, in which said set of CDRs comprises SEQ ID NO:20, 22 or 24 and (b) a set of four framework regions, in which said set of framework regions differs from the set of framework regions in monoclonal antibody HeFi-1, and in which said antibody or derivative thereof immunospecifically binds CD30.

In a specific embodiment, the invention encompasses an antibody or derivative thereof comprising a light chain variable domain, said variable domain comprising (a) a set of three CDRs, in which said set of CDRs comprises SEQ ID NO:12, 14 or 16, and (b) a set of four framework regions, in which said set of framework regions differs from the set of framework regions in monoclonal antibody AC10, and in which said antibody or derivative thereof immunospecifically binds CD30.

In a specific embodiment, the invention encompasses an antibody or derivative thereof comprising a light chain variable domain, said variable domain comprising (a) a set of three CDRs, in which said set of CDRs comprises SEQ ID NO:28, 30, or 32, and (b) a set of four framework regions, in which said set of framework regions differs from the set of framework regions in monoclonal antibody HeFi-1, and in which said antibody or derivative thereof immunospecifically binds CD30.

Additionally, antibodies of the present invention may also be described or specified in terms of their primary structures. Antibodies having at least 50%, at least 55%, at least 60%, at least 65%, at least 70%, at least 75%, at least 80%, at least 85%, at least 90%, at least 95% and most preferably at least 98% identity (as calculated using methods known in the art and described herein) to the variable regions and AC10 or HeFi-1 are also included in the present invention. Antibodies of the present invention may also be described or specified in terms of their binding affinity to CD30. Preferred binding affinities include those with a dissociation constant or Kd less than $5\times10^2$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10-6$ M, $5\times10^{-7}$ M, $10^{-7}$ M, $5\times10^{-8}$ M, $10^{-8}$M, $5\times10^{-9}$M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The antibodies of the invention include derivatives that are modified, i.e, by the covalent attachment of any type of molecule to the antibody such that covalent attachment does not prevent the antibody from binding to CD30 or from exerting a cytostatic or cytotoxic effect on HD cells. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to CD30 can be produced by various procedures well known in the art. For example, CD30 can be administered to various host animals including, but not limited to, rabbits, mice, rats, etc. to induce the production of sera containing polyclonal antibodies specific for the protein. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed., 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with CD30 or a cell expressing CD30 or a fragment or derivative thereof. Once an immune response is detected, e.g., antibodies specific for CD30 are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding CD30. Ascites fluid, which generally contains high levels of antibodies, can be generated by injecting mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind to CD30.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH 1 domain of the heavy chain.

For example, the antibodies of the present invention can also be generated using various phage display methods known in the art. In phage display methods, functional antibody domains are displayed on the surface of phage particles which carry the nucleic acid sequences encoding them. In a particular embodiment, such phage can be utilized to display antigen binding domains expressed from a repertoire or combinatorial antibody library (e.g., human or murine). In phage display methods, functional antibody domains are displayed on the surface of phage particles which carry the nucleic acid sequences encoding them. In particular, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 binding domains expressed from phage with Fab, Fv or disulfide stabilized Fv antibody domains recombinantly fused to either the phage gene III or gene VIII protein. Phage expressing an antigen binding domain that binds to CD30 or an AC10 or HeFi-binding portion thereof can be selected or identified with antigen e.g., using labeled antigen or antigen bound or captured to a solid surface or bead. Examples of phage display methods that can be used to make the antibodies of the present invention include those disclosed in Brinkman et al., 1995, J. Immunol. Methods 182:41–50; Ames et al., 1995, J. Immunol. Methods 184:177–186; Kettleborough et al., 1994, Eur. J. Immunol. 24:952–958; Persic et al., 1997, Gene 187:9–18; Burton et al., 1994, Advances in Immunology, 191–280; PCT Application No. PCT/GB91/O1 134; PCT Publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5;580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 1992, 12(6):864–869; and Sawai et al, 1995, AJRI 34:26–34; and Better et al., 1988, Science 240:1041–1043 (said references incorporated by reference in their entireties).

Examples of techniques which can be used to produce single-chain Fvs and antibodies include those described in U.S. Pat. Nos. 4,946,778 and 5,258,498; Huston et al., 1991, Methods in Enzymology 203:46–88; Shu et al., 1993, PNAS 90:7995–7999; and Skerra et al., 1988, Science 240:1038–1040. For some uses, including in vivo use of antibodies in humans and in vitro proliferation or cytotoxicity assays, it is preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science, 1985, 229:1202; Oi et al., 1986, BioTechniques 4:214; Gillies et al., 1989, J. Immunol. Methods 125:191–202: U.S. Pat. Nos. 5,807,715; 4,816,567; and 4,816,397, which are incorporated herein by reference in their entirety. Humanized antibodies are antibody molecules from non-human species antibody that binds the desired antigen having one or more CDRs from the non-human species and framework and constant regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., 1988, Nature 332:323, which are incorporated herein by reference in their entireties.) Antibodies can be humanized using a variety of techniques known in the art including, for example, CDR-grafting (EP 239,400; PCT publication WO 9 1/09967; U.S. Pat. Nos. 5,225,539; 5,530,101; and 5,585, 089), veneering or resurfacing (EP 592,106; EP 519,596; Padlan, Molecular Immunology, 1991, 28(4/5):489–498; Studnicka et al., 1994, Protein Engineering 7(6):805–814; Roguska. et al., 1994, PNAS 91:969–973), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which express human immunoglobulin genes. For example, the human heavy and light chain immunoglobulin gene complexes may be introduced randomly or by homologous recombination into mouse embryonic stem cells. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of CD30. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, Lonberg and Huszar, 1995, Int. Rev. Immunol. 13:65–93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1994, Bio/technology 12:899–903).

Further, antibodies to CD30 can, in turn, be utilized to generate anti-idiotype antibodies that "mimic" proteins of the invention using techniques well known to those skilled in the art. (See, e.g., Greenspan & Bona, 1989, FASEB J. 7(5):437–444; and Nissinoff, 1991, J. Immunol. 147(8): 2429–2438). Fab fragments of such anti-idiotypes can be used in therapeutic regimens to elicit an individual's own immune response against CD30 and HD cells.

As alluded to above, proteins that are therapeutically or prophylactically useful against HD need not be antibodies. Accordingly, proteins of the invention may comprise one or more CDRs from an antibody that binds to CD30 and exerts a cytotoxic and/or cytostatic effect on HD cells. Preferably, a protein of the invention is a multimer, most preferably a dimer.

The invention also provides proteins, including but not limited to antibodies, that competitively inhibit binding of AC10 or HeFi-1 to CD30 as determined by any method known in the art for determining competitive binding, for example, the immunoassays described herein. In preferred embodiments, the protein competitively inhibits binding of AC10 or HeFi-1 to CD30 by at least 50%, more preferably at least 60%, yet more preferably at least 70%, and most preferably at least 75%. In other embodiments, the protein competitively inhibits binding of AC10 or HeFi-1 to CD30 by at least 80%, at least 85%, at least 90%, or at least 95%.

As discussed in more detail below, the proteins of the present invention may be used either alone or in combination with other compositions in the prevention or treatment of HD. The proteins may further be recombinantly fused to a heterologous protein at the N- or C-terminus or chemically conjugated (including covalently and non-covalently conjugations) to cytotoxic agents, proteins or other compositions. For example, antibodies of the present invention may be recombinantly fused or conjugated to molecules useful as chemotherapeutics or toxins, or comprise a radionuclide for use as a radio-therapeutic. See, e.g., PCT publications WO 92/08495; WO 91/14438; WO 89/12624; U.S. Pat. No. 5,314,995; and EP 396,387.

Proteins of the invention may be produced recombinantly by fusing the coding region of one or more of the CDRs of an antibody of the invention in frame with a sequence coding for a heterologous protein. The heterologous protein may provide one or more of the following characteristics: added therapeutic benefits; promote stable expression of the protein of the invention; provide a means of facilitating high yield recombinant expression of the protein of the invention; or provide a multimerization domain.

In addition to proteins comprising one or more CDRs of an antibody of the invention, proteins of the invention may be identified using any method suitable for screening for protein—protein interactions. Initially, proteins are identified that bind to CD30, then their ability to exert a cytostatic or cytotoxic effect on HD cells can be determined. Among the traditional methods which can be employed are "interaction cloning" techniques which entail probing expression libraries with labeled CD30 in a manner similar to the technique of antibody probing of λgt11 libraries, supra. By way of example and not limitation, this can be achieved as follows: a cDNA clone encoding CD30 (or an AC10 or HeFi-1 binding domain thereof) is modified at the terminus by inserting the phosphorylation site for the heart muscle kinase (HMK) (Blanar & Rutter, 1992, Science 256:1014–1018). The recombinant protein is expressed in $E.$ $coli$ and purified on a GDP-affinity column to homogeneity (Edery et al., 1988, Gene 74:517–525) and labeled using $\gamma^{32}$P-ATP and bovine heart muscle kinase (Sigma) to a specific activity of $1\times10^8$ cpm/µg, and used to screen a human placenta λgt11 cDNA library in a "far-Western assay" (Blanar & Rutter, 1992, Science 256:1014–1018). Plaques which interact with the CD30 probe are isolated. The cDNA inserts of positive λ plaques are released and subcloned into a vector suitable for sequencing, such as pBluescript KS (Stratagene).

One method which detects protein interactions in vivo, the two-hybrid system, is described in detail for illustration purposes only and not by way of limitation. One version of this system has been described (Chien et al., 1991, Proc. Natl. Acad. Sci. USA, 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to CD30, and the other consists of the activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the transcription activator's binding sites. Either hybrid protein alone cannot activate transcription of the reporter gene, the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with CD30, which in this context is a "bait" gene product. Total genomic or cDNA sequences are fused to the DNA encoding an activation domain. This library and a plasmid encoding a hybrid of a CD30 coding region (for example, a nucleotide sequence which codes for a domain of CD30 known to interact with HeFi-1 or AC10) fused to the DNA-binding domain are co-transformed into a yeast reporter strain, and the resulting transformants are screened for those that express the reporter gene. For example, and not by way of limitation, the CD30 coding region can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

Once a CD30-binding protein is identified, its ability (alone or when multimerized or fused to a dimerization or multimerization domain) to elicit a cytostatic or cytotoxic effect on HD cells is determined by contacting a culture of an HD cell line, such as L428, L450, HDLM2 or KM-H2, with the protein. Culture conditions are most preferably about 5,000 cells in a culture area of about 0.33 cm$^2$, and the contacting period being approximately 72 hours. The culture is then exposed to 0.5 µCi of $^3$H-thymidine during the final 8 hours of the 72-hour period and the incorporation of $^3$H-thymidine into cells of the culture is measured. The protein has a cytostatic or cytotoxic effect on the HD cell line if the cells of the culture have reduced $^3$H-thymidine incorporation compared to cells of the same cell line cultured under the same conditions but not contacted with the protein.

Without limitation as to mechanism of action, a protein of the invention preferably has more than one CD30-binding site and therefore a capacity to cross link CD30 molecules. Proteins which bind to CD30 or compete for binding to CD30 with AC10 or HeFi-1 can acquire the ability to induce cytostatic or cytotoxic effects on HD cells if dimerized or multimerized. Wherein the CD30-binding protein is a monomeric protein, it can be expressed in tandem, thereby resulting in a protein with multiple CD30 binding sites. The CD30-binding sites can be separated by a flexible linker region. In another embodiment, the CD30-binding proteins can be chemically cross-linked, for example using gluteraldehyde, prior to administration. In a preferred embodiment, the CD30-binding region is fused with a heterologous protein, wherein the heterologous protein comprises a dimerization and multimerization domain. Prior to administration of the protein of the invention to a subject for the purpose of treating or preventing HD, such a protein is subjected to conditions that allows formation of a homodimer or heterodimer. A heterodimer, as used herein, may comprise identical dimerization domains but different CD30-binding regions, identical CD30-binding regions but different dimerization domains, or different CD30-binding regions and dimerization domains.

Particularly preferred dimerization domains are those that originate from transcription factors.

In one embodiment, the dimerization domain is that of a basic region leucine zipper ("bZIP"). bZIP proteins characteristically possess two domains—a leucine zipper structural domain and a basic domain that is rich in basic amino acids, separated by a "fork" domain (C. Vinson et al., 1989, Science, 246:911–916). Two bZIP proteins dimerize by forming a coiled coil region in which the leucine zipper domains dimerize. Accordingly, these coiled coil regions may be used as fusion partners for the proteins and the invention.

Particularly useful leucine zipper domain are those of the yeast transcription factor GCN4, the mammalian transcription factor CCAAT/enhancer-binding protein C/EBP, and the nuclear transform in oncogene products, Fos and Jun (see Landschultz et al., 1988, Science 240:1759–1764; Baxevanis and Vinson, 1993, Curr. Op. Gen. Devel., 3:278–285; and O'Shea et al., 1989, Science, 243:538–542).

In another embodiment, the dimerization domain is that of a basic-region helix-loop-helix ("bHLH") protein (Murre et al, 1989, Cell, 56:777–783). bHLH proteins are also composed of discrete domains, the structure of which allows them to recognize and interact with specific sequences of DNA. The helix-loop-helix region promotes dimerization through its amphipathic helices in a fashion analogous to that of the leucine zipper region of the bZIP proteins (Davis et al., 1990 Cell, 60:733–746; Voronova and Baltimore, 1990 Proc. Natl. Acad. Sci. USA, 87:4722–4726). Particularly useful hHLH proteins are myc, max, and mac.

Heterodimers are known to form between Fos and Jun (Bohmann et al., 1987, Science, 238:1386–1392), among members of the ATF/CREB family (Hai et al., 1989, Genes Dev., 3:2083–2090), among members of the C/EBP family (Cao et al., 1991, Genes Dev., 5:1538–1552; Williams et al., 1991, Genes Dev., 5:1553–1567; and Roman et al., 1990, Genes Dev., 4:1404–1415), and between members of the ATF/CREB and Fos/Jun families Hai and Curran, 1991, Proc. Natl. Acad. Sci. USA, 88:3720–3724). Therefore, when a protein of the invention is administered to a subject as a heterodimer comprising different dimerization domains, any combination of the foregoing may be used.

5.2 Binding Assays

As described above, the proteins, including antibodies, of the invention bind to CD30 and exert a cytostatic or cytotoxic effect on HD cells. Methods of demonstrating the ability of a protein of the invention to bind to CD30 are described herein.

The antibodies of the invention may be assayed for immunospecific binding to CD30 by any method known in the art. The immunoassays which can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et. al., eds., 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody to the cell lysate, incubating for a period of time (e.g., 1–4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody to immunoprecipitate CD30 can be assessed by, e.g., Western blot analysis. One of skill in the art would be knowledgeable as to the parameters that can be modified to increase the binding of the antibody to CD30 and decrease the background (e.g., pre-clearing the cell lysate with sepharose beads). For further discussion regarding immunoprecipitation protocols see, e.g., Ausubel et al., eds., 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, incubating the membrane in blocking solution (e.g., PBS with 3% BSA or non-fat milk), washing the membrane in washing buffer (e.g., PBS-Tween 20), blocking the membrane with primary antibody (i.e., the putative anti-CD30 antibody) diluted in blocking buffer, washing the membrane in washing buffer, incubating the membrane with a secondary antibody (which recognizes the primary antibody, e.g., an anti-human antibody) conjugated to an enzyme substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the secondary antibody. One of skill in the art would be knowledgeable as to the parameters that can be modified to increase the signal detected and to reduce the background noise. For further discussion regarding Western blot protocols see, e.g., Ausubel et al., eds., 1994, Current Protocols in Molecular Biology, Vol. 1, John Wiley & Sons, Inc., New York at 10.8.1.

ELISAs comprise preparing antigen (i.e., CD30), coating the well of a 96 well microtiter plate with the CD30, adding the antibody conjugated to a detectable compound such as an enzyme (e.g., horseradish peroxidase or alkaline phosphatase) to the well and incubating for a period of time, and detecting the presence of the antibody. In ELISAs the antibody does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of CD30 protein to the coated well. One of skill in the art would be knowledgeable as to the parameters that can be modified to increase the signal detected as well as other variations of ELISAs known in the art. For further discussion regarding ELISAs see, e.g., Ausubel et al., eds., 1994, Current Protocols in Molecular Biology, Vol. 1, John Wiley & Sons, Inc., New York at 11.2.1.

The binding affinity of an antibody to CD30 and the off-rate of an antibody CD30 interaction can be determined by competitive binding assays. One example of a competitive binding assay is a radioimmunoassay comprising the incubation of labeled CD30 (e.g., $^3H$ or $^{125}I$) with the antibody of interest in the presence of increasing amounts of unlabeled CD30, and the detection of the antibody bound to the labeled CD30. The affinity of the antibody for CD30 and the binding off-rates can then be determined from the data by Scatchard plot analysis. Competition with a second antibody (such as AC10 or HeFi-1) can also be determined using radioimmunoassays. In this case, CD30 is incubated with the antibody of interest conjugated to a labeled compound (e.g., $^3H$ or $^{125}I$) in the presence of increasing amounts of an unlabeled second antibody.

Proteins of the invention may also be assayed for their ability to bind to CD30 by a standard assay known in the art. Such assays include far Westerns and the yeast two hybrid system. These assays are described in Section 5.2, supra. Another variation on the far Western technique described above entails measuring the ability of a labeled candidate protein to bind to CD30 in a Western blot. In one non-limiting example of a far Western blot, CD30 or the fragment thereof of interest is expressed as a fusion protein further comprising glutathione-S-transferase (GST) and a protein serine/threonine kinase recognition site (such as a cAMP-dependent kinase recognition site). The fusion protein is purified on glutathione-Sepharose beads (Pharmacia Biotech) and labeled with bovine heart kinase (Sigma) and 100 µCi of $^{32}P$-ATP (Amersham). The test protein(s) of interest are separated by SDS-PAGE and blotted to a nitrocellulose membrane, then incubated with the labeled CD30. Thereafter, the membrane is washed and the radioactivity quantitated. Conversely, the protein of interest can be labeled by the same method and used to probe a nitrocellulose membrane onto which CD30 has been blotted.

5.3 Assays for Cytotoxic and Cytostatic Activities

By definition, a protein of the invention must exert a cytostatic or cytotoxic effect on a cell of HD. Suitable HD cell lines for this purpose include L428, L450, HDLM2 and KM-H2 (all of which are available from the German Collection of Microorganisms and Cell Cultures (DMSZ: Deutsche Sammlung von Mikroorganismen und Zellkulturen GmbH)).

Many methods of determining whether a protein exerts a cytostatic or cytotoxic effect on a cell are known to those of skill in the art, and can be used to elucidate whether a particular protein is a protein of the invention. Illustrative examples of such methods are described below.

Wherein a protein that binds to CD30 does not exert a cytostatic or cytotoxic effect on HD cells, the protein can be multimerized according to the methods described in Section 5.1, supra, and the multimer assayed for its ability to exert a cytostatic or cytotoxic effect on HD cells.

Once a protein is identified that both (i) binds to CD30 and (ii) exerts a cytostatic or cytotoxic effect on HD cells, its therapeutic value is validated in an animal model, as described in Section 6, infra.

In a preferred embodiment, determining whether a protein exerts a cytostatic or cytotoxic effect on a HD cell line can be made by contacting a 5,000 cell-culture of the HD cell line in a culture area of about 0.33 cm² with the protein for a period of 72 hours. During the last 8 hours of the 72-hour period, the culture is exposed to 0.5 μCi of $^3$H-thymidine. The incorporation of $^3$H-thymidine into cells of the culture is then measured. The protein has a cytostatic or cytotoxic effect on the HD cell line and is useful for the treatment or prevention of HD if the cells of the culture contacted with the protein have reduced $^3$H-thymidine incorporation compared to cells of the same HD cell line cultured under the same conditions but not contacted with the anti-CD30 antibody.

There are many cytotoxicity assays known to those of skill in the art. Some of these assays measure necrosis, while others measure apoptosis (programmed cell death). Necrosis is accompanied by increased permeability of the plasma membrane; the cells swell and the plasma membrane ruptures within minutes. On the other hand, apoptosis is characterized by membrane blebbing, condensation of cytoplasm and the activation of endogenous endonucleases. Only one of these effects on HD cells is sufficient to show that a CD30-binding protein is useful in the treatment or prevention of HD as an alternative to the assays measuring cytostatic or cytotoxic effects described above.

In one embodiment, necrosis measured by the ability or inability of a cell to take up a dye such as neutral red, trypan blue, or ALAMAR™ blue (Page et al., 1993, Intl. J. of Oncology 3:473–476). In such an assay, the cells are incubated in media containing the dye, the cells are washed, and the remaining dye, reflecting cellular uptake of the dye, is measured spectrophotometrically.

In another embodiment, the dye is sulforhodamine B (SRB), whose binding to proteins can be used as a measure of cytotoxicity (Skehan et al., 1990, J. Nat'l Cancer Inst. 82:1107–12).

In yet another embodiment, a tetrazolium salt, such as MTT, is used in a quantitative colorimetric assay for mammalian cell survival and proliferation by detecting living, but not dead, cells (see, e.g., Mosmann, 1983, J. Immunol. Methods 65:55–63).

In yet another embodiment, apoptotic cells are measured in both the attached and "floating" compartments of the cultures. Both compartments are collected by removing the supernatant, trypsinizing the attached cells, and combining both preparations following a centrifugation wash step (10 minutes, 2000 rpm). The protocol for treating tumor cell cultures with sulindac and related compounds to obtain a significant amount of apoptosis has been described in the literature (see, e.g., Piazza et al., 1995, Cancer Research 55:3110–16). Features of this method include collecting both floating and attached cells, identification of the optimal treatment times and dose range for observing apoptosis, and identification of optimal cell culture conditions.

In yet another embodiment, apoptosis is quantitated by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica, 1999, no. 2, pp. 34–37 (Roche Molecular Biochemicals).

In yet another embodiment, apoptosis can be observed morphologically.

Following treatment with a test protein or nucleic acid, cultures can be assayed for apoptosis and necrosis by fluorescent microscopy following labeling with acridine orange and ethidium bromide. The method for measuring apoptotic cell number has previously been described by Duke & Cohen, 1992, Current Protocols In Immunology, Coligan et al., eds., 3.17.1–3.17.16. In another mode of the embodiment, cells can be labeled with the DNA dye propidium iodide, and the cells observed for morphological changes such as chromatin condensation and margination along the inner nuclear membrane, cytoplasmic condensation, increased membrane blebbing and cellular shrinkage.

5.4 Nucleic Acids of the Invention

The invention further provides nucleic acids comprising a nucleotide sequence encoding a protein, including but not limited to, a protein of the invention and fragments thereof. Nucleic acids of the invention preferably encode one or more CDRs of antibodies that bind to CD30 and exert cytotoxic or cytostatic effects on HD cells. Exemplary nucleic acids of the invention comprise SEQ ID NO:3, SEQ ID NO:5, SEQ ID NO:7, SEQ ID NO:11, SEQ ID NO:13, SEQ ID NO:15, SEQ ID NO:19, SEQ ID NO:21, SEQ ID NO:23, SEQ ID NO:27, SEQ ID NO:29 or SEQ ID NO:31. Preferred nucleic acids of the invention comprise SEQ ID NO:1, SEQ ID NO:9, SEQ ID NO:17, or SEQ ID NO:25. (See Table 1 at pages 9–10, supra, for identification of the domain of AC10 or HeFi-1 to which these sequence identifiers correspond).

The invention also encompasses nucleic acids that hybridize under stringent, moderate or low stringency hybridization conditions, to nucleic acids of the invention, preferably, nucleic acids encoding an antibody of the invention.

By way of example and not limitation, procedures using such conditions of low stringency for regions of hybridization of over 90 nucleotides are as follows (see also Shilo and Weinberg, 1981, Proc. Natl. Acad. Sci. U.S.A. 78,:6789–6792). Filters containing DNA are pretreated for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and re-exposed to film. Other conditions of low stringency which may be used are well known in the art (e.g., as employed for cross-species hybridizations).

Also, by way of example and not limitation, procedures using such conditions of high stringency for regions of hybridization of over 90 nucleotides are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in prehybridization mixture containing 100 μg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography.

Other conditions of high stringency which may be used depend on the nature of the nucleic acid (e.g. length, GC content, etc.) and the purpose of the hybridization (detection, amplification, etc.) and are well known in the art. For example, stringent hybridization of a nucleic acid of approximately 15–40 bases to a complementary sequence in the polymerase chain reaction (PCR) is done under the following conditions: a salt concentration of 50 mM KCl, a buffer concentration of 10 mM Tris-HCl, a $Mg^{2+}$ concentration of 1.5 mM, a pH of 7–7.5 and an annealing temperature of 55–60° C.

In another specific embodiment, a nucleic acid which is hybridizable to a nucleic acid of the invention acid, or its complement, under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987–1997, Current Protocols, © 1994–1997 John Wiley and Sons, Inc.).

The nucleic acids of the invention may be obtained, and the nucleotide sequence of the nucleic acids determined, by any method known in the art. For example, if the nucleotide sequence of the protein is known, a nucleic acid encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the protein, annealing and ligating of those oligonucleotides, and then amplification of the ligated oligonucleotides by PCR.

Alternatively, a nucleic acid encoding a protein of the invention may be generated from nucleic acid from a suitable source. If a clone containing a nucleic acid encoding a particular protein is not available, but the sequence of the protein molecule is known, a nucleic acid encoding the protein may be chemically synthesized or obtained from a suitable source (e.g., a cDNA library such as an antibody cDNA library or a cDNA library generated from, or nucleic acid, preferably poly A+ RNA, isolated from, any tissue or cells expressing the protein. If the protein is an antibody, the library source can be hybridoma cells selected to express the antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the protein. Amplified nucleic acids generated by PCR may then be cloned into replicable cloning vectors using any method well known in the art.

Once the nucleotide sequence and corresponding amino acid sequence of the antibody is determined, the nucleotide sequence of the protein may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the protein is an antibody, and the amino acid sequence of the heavy and/or light chain variable domains may be inspected to identify the sequences of the CDRs by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and are preferably human framework regions (see, e.g., Chothia et al., 1998, J. Mol. Biol. 278:457–479 for a listing of human framework regions). The nucleic acid generated by the combination of the framework regions and CDRs encodes an antibody that specifically binds CD30 and exerts a cytostatic and/or cytotoxic effect on HD cells. Preferably, as discussed supra, one or more amino acid substitutions may be made within the framework regions, and, preferably, the amino acid substitutions improve binding of the antibody to CD30 and/or to enhance the cytostatic and/or cytotoxic effect of the antibody. Additionally, such methods may be used to make amino acid substitutions or deletions of one or more variable region cysteine residues participating in an intrachain disulfide bond to generate antibody molecules lacking one or more intrachain disulfide bonds. Other alterations to the nucleic acid are encompassed by the present invention and within the skill of the art.

In addition, techniques developed for the production of "chimeric antibodies" (Morrison et al., 1984, Proc. Natl. Acad. Sci. 81:851–855; Neuberger et al., 1984, Nature 312:604–608; Takeda et al., 1985, Nature 314:452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, 1988, Science 242:423–42; Huston et al., 1988, Proc. Natl. Acad. Sci. USA 85:5879–5883; and Ward et al., 1989, Nature 334:544–54) can be adapted to produce single chain antibodies. Single chain antibodies are formed by linking the heavy and light chain fragments of the Fv region via an amino acid bridge, resulting in a single chain protein. Techniques for the assembly of functional Fv fragments in E. coli may also be used (Skerra et al., 1988, Science 242:1038–1041).

5.5 Sequences Related to AC10 and HeFi-1

The present invention further encompasses proteins and nucleic acids comprising a region of homology to CDRs of AC10 and HeFi-1, or the coding regions therefor, respectively. In various embodiments, the region of homology is characterized by at least 50%, at least 55%, at least 60%, at least 65%, at least 70%, at least 75%, at least 80%, at least 85%, at least 90%, at least 95% or at least 98% identity with the corresponding region of AC10 or HeFi-1.

In one embodiment, the present invention provides a protein with a region of homology to a CDR of HeFi-1 (SEQ ID NO:20, SEQ ID NO:22; SEQ ID NO:24; SEQ ID NO:28, SEQ ID NO:30 or SEQ ID NO:32). In another embodiment, the present invention provides a protein with a region of homology to a CDR of AC10 (SEQ ID NO:4; SEQ ID NO:6; SEQ ID NO:8; SEQ ID NO:12; SEQ ID NO:14; or SEQ ID NO:16).

In another embodiment, the present invention provides a nucleic acid with a region of homology to a CDR coding region of HeFi-1 (SEQ ID NO:19, SEQ ID NO:21, SEQ ID NO:23, SEQ ID NO:27, SEQ ID NO:29 or SEQ ID NO:31). In yet another embodiment, the present invention provides a nucleic acid with a region of homology to a CDR coding region of AC10 (SEQ ID NO:3, SEQ ID NO:5, SEQ ID NO:7, SEQ ID NO:1, SEQ ID NO:13, SEQ ID NO:15).

The present invention further encompasses proteins and nucleic acids comprising a region of homology to the variable regions of AC10 and HeFi-1, or the coding region therefor, respectively. In various embodiments, the region of homology is characterized by at least 50%, at least 55%, at least 60%, at least 65%, at least 70%, at least 75%, at least 80%, at least 85%, at least 90%, at least 95% or at least 98% identity with the corresponding region of AC10 or HeFi-1.

In one embodiment, the present invention provides a protein with a region of homology to a variable region of HeFi-1 (SEQ ID NO:18 or SEQ ID NO:26). In another embodiment, the present invention provides a protein with a region of homology to a variable region of AC10 (SEQ ID NO: 2 or SEQ ID NO: 10).

In one embodiment, the present invention provides a nucleic acid with a region of homology to a variable region coding region of HeFi-1(SEQ ID NO:17 or SEQ ID NO:25). In another embodiment, the present invention provides a nucleic with a region of homology to a variable region coding region of AC10 (SEQ ID NO:1 or SEQ ID NO:9).

To determine the percent identity of two amino acid sequences or of two nucleic acids, e.g. between the sequences of an AC10 or HeFi-1 variable region and sequences from other proteins with regions of homology to the AC10 or HeFi-1 variable region, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment, the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 90:5873–5877. Such an algorithm is incorporated into the NBLAST and the XBLAST programs of Altschul, et al., 1990, J. Mol. Biol. 215:403–410. BLAST nucleotide searches can be performed with the NBLAST program, score=100, wordlength=12 to obtain nucleotide sequences homologous to a nucleic acid encoding a SCA-1 modifier protein. BLAST protein searches can be performed with the XBLAST program, score=50, wordlength=3 to obtain amino acid sequences homologous to SCA-1 modifier protein. To obtain gapped alignments for comparison purposes, Gapped BLAST can be utilized as described in Altschul et al., 1997, Nucleic Acids Res. 25:3389–3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci., 10:3–5; and FASTA described in Pearson and Lipman, 1988, Proc. Natl. Acad. Sci. 85:2444–8. Within FASTA, ktup is a control option that sets the sensitivity and speed of the search. If ktup=2, similar regions in the two sequences being compared are found by looking at pairs of aligned residues; if ktup=1, single aligned amino acids are examined. Ktup can be set to 2 or 1 for protein sequences, or from 1 to 6 for DNA sequences. The default if ktup is not specified is 2 for proteins and 6 for DNA.

Alternatively, protein sequence alignment may be carried out using the CLUSTAL W algorithm, as described by Higgins et al., 1996, Methods Enzymol. 266:383–402.

The percent identity between two sequences can be determined using techniques similar to those described above, with or without allowing gaps. In calculating percent identity, only exact matches are counted.

5.6 Methods of Producing the Proteins of the Invention

The proteins, including antibodies, of the invention can be produced by any method known in the art for the synthesis of proteins, in particular, by chemical synthesis or preferably, by recombinant expression techniques.

Recombinant expression of a protein of the invention, including a fragment, derivative or analog thereof, (e.g., a heavy or light chain of an antibody of the invention) requires construction of an expression vector containing a nucleic acid that encodes the protein. Once a nucleic acid encoding a protein of the invention has been obtained, the vector for the production of the protein molecule may be produced by recombinant DNA technology using techniques well known in the art. Thus, methods for preparing a protein by expressing a nucleic acid containing nucleotide sequence encoding said protein are described herein. Methods which are well known to those skilled in the art can be used to construct expression vectors containing coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding a protein of the invention operably linked to a promoter. Wherein the protein is an antibody, the nucleotide sequence may encode a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce a protein of the invention. Thus, the invention encompasses host cells containing a nucleic acid encoding a protein of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the proteins molecules of the invention. Such host-expression systems represent vehicles by which the coding sequences of interest may be produced and subsequently purified, but also represent cells which may, when transformed or transfected with the appropriate nucleotide coding sequences, express a protein of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as Escherichia coli, and more preferably, eukaryotic cells, especially for the expression of whole recombinant antibody molecules, are used for the expression of a recombinant protein of the invention. For example, mammalian cells such as Chinese hamster ovary cells (CHO), in conjunction with a vector such as the major intermediate early gene promoter element from human cytomegalovirus is an effective expression system for proteins of the invention (Foecking et al., 1986, Gene 45:101; Cockett et al., 1990, Bio/Technology 8:2).

In bacterial systems, a number of expression vectors may be advantageously selected depending upon the use intended for the folding and post-translation modification requirements protein being expressed. Where possible, when a large quantity of such a protein is to be produced, for the generation of pharmaceutical compositions comprising a protein of the invention, vectors which direct the expression of high levels of fusion protein products that are readily purified may be desirable. Such vectors include, but are not limited, to the E. coli expression vector pUR278 (Ruther et al., 1983, EMBO 1. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 24:5503–5509); and the like. pGEX vectors may also be used to express fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the coding sequence of the protein of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the protein of the invention in infected hosts. (See, e.g., Logan & Shenk, 1984, Proc. Natl. Acad. Sci. USA 8 1:355–359). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein of the invention. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, Hela, COS, MDCK, 293, 3T3, and W138.

For long-term, high-yield production of recombinant proteins, stable expression is preferred. For example, cell lines which stably express the protein of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the protein of the invention.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1992, Proc. Natl. Acad. Sci. USA 48:202), and adenine phosphoribosyltransferase (Lowy et al., 1980, Cell 22:8–17) genes can be employed in tk-, hgprt- or aprt-cells, respectively. Also, antimetabolite resistance can be used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62: 191–217; May, 1993, TIB TECH 11(5):155–215); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, J. Mol. Biol. 150:1, which are incorporated by reference herein in their entireties.

The expression levels of a protein of the invention can be increased by vector amplification (for a review, see Bebbington and Hentschel, "The Use of Vectors Based on Gene Amplification for the Expression of Cloned Genes in Mammalian Cells in DNY Cloning", Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the protein of the invention will also increase (Crouse et al., 1983, Mol. Cell. Biol. 3:257).

Wherein the protein of the invention is an antibody, the host cell may be co-transfection with two expression vectors of the invention, the first vector encoding a heavy chain derived protein and the second vector encoding a light chain derived protein. The two vectors may contain identical selectable markers which enable equal expression of heavy and light chain proteins. Alternatively, a single vector may be used which encodes, and is capable of expressing, both heavy and light chain proteins. In such situations, the light chain should be placed before the heavy chain to avoid an excess of toxic free heavy chain (Proudfoot, 1986, Nature 322:52 (1986); Kohler, 1980, Proc. Natl. Acad. Sci. USA 77:2 197). The coding sequences for the heavy and light chains may comprise cDNA or genomic DNA.

Once a protein molecule of the invention has been produced by an animal, chemically synthesized, or recombinantly expressed, it may be purified by any method known in the art for purification of proteins, for example, by chromatography (e.g., ion exchange; affinity, particularly by affinity for the specific antigen, Protein A (for antibody molecules, or affinity for a heterologous fusion partner wherein the protein is a fusion protein; and sizing column chromatography), centrifugation, differential solubility, or by any other standard technique for the purification of proteins.

The present invention encompasses CD3-binding proteins recombinantly fused or chemically conjugated (including both covalent and non-covalent conjugation) to heterologous proteins (of preferably at least 10, 20, 30, 40, 50, 60, 70, 80, 90 or at least 100 amino acids) of the present invention to generate fusion proteins. The fusion does not necessarily need to be direct, but may occur through linker sequences.

The present invention further includes compositions comprising proteins of the invention fused or conjugated to antibody domains other than the variable regions. For example, the proteins of the invention may be fused or conjugated to an antibody Fc region, or portion thereof. The antibody portion fused to a protein of the invention may comprise the constant region, hinge region, CH 1 domain, CR2 domain, and CH3 domain or any combination of whole domains or portions thereof. The proteins may also be fused or conjugated to the above antibody portions to form multimers. For example, Fc portions fused to the proteins of the invention can form dimers through disulfide bonding between the Fc portions. Higher multimeric forms can be made by fusing the proteins to portions of IgA and IgM. Methods for fusing or conjugating the proteins of the invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 9 1/06570; Ashkenazi et al., 1991, Proc. Nat. Acad. Sci. USA 88:10535–10539; Zheng et al., 1995, J. Immunol. 154:5590–5600; and Vil et al., 1992, Proc. Natl. Acad. Sci. USA 89:11337–11341 (said references incorporated by reference in their entireties).

5.7 Conjugates and Fusion Proteins

As discussed, supra, the proteins of the invention encompass proteins that bind to CD30 and exert a cytostatic and/or cytotoxic effect on HD cells, and that are further fused or conjugated to heterologous proteins or cytotoxic agents.

The present invention thus provides for treatment of Hodgkin's Disease by administration of a protein or nucleic acid of the invention. Proteins of the invention include but are not limited to: AC10 and HeFi-1 proteins, antibodies and analogs and derivatives thereof (e.g., as described herein above); the nucleic acids of the invention include but are not limited to nucleic acids encoding such AC10 and HeFi-1 proteins, antibodies and analogs or derivatives (e.g., as described herein above).

In certain embodiments of the invention, a protein or nucleic acid of the invention may be chemically modified to improve its cytotoxic and/or cytostatic properties. For example, a protein of the invention can be administered as a conjugate. Particularly suitable moieties for conjugation to proteins of the invention are chemotherapeutic agents, pro-drug converting enzymes, radioactive isotopes or compounds, or toxins. Alternatively, a nucleic acid of the invention may be modified to functionally couple the coding sequence of a pro-drug converting enzyme with the coding sequence of a protein of the invention, such that a fusion protein comprising the functionally active pro-drug converting enzyme and protein of the invention is expressed in the subject upon administration of the nucleic acid in accordance with the gene therapy methods described in Section 5.7, infra.

In one embodiment, a protein of the invention is fused to a marker sequence, such as a peptide, to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821–824, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., 1984, Cell 37:767) and the "flag" tag. Such fusion proteins can be generated by standard recombinant methods known to those of skill in the art.

In another embodiment, the proteins of the invention are fused or conjugated to a therapeutic agent. For example, a protein of the invention may be conjugated to a cytotoxic agent such as a chemotherapeutic agent, a toxin (e.g., a cytostatic or cytocidal agent), or a radionuclide (e.g., alpha-emitters such as, for example, $^{212}$Bi, $^{211}$At, or beta-emitters such as, for example, $^{131}$I, $^{90}$Y, or $^{67}$Cu).

Drugs such as methotrexate (Endo et al., 1987, Cancer Research 47:1076–1080), daunomycin (Gallego et al., 1984, Int. J. Cancer. 33:737–744), mitomycin C (MMC) (Ohkawa et al., 1986, Cancer Immunol. Immunother. 23:81–86) and vinca alkaloids (Rowland et al., 1986, Cancer Immunol Immunother. 21:183–187) have been attached to antibodies and the derived conjugates have been investigated for antitumor activities. Care should be taken in the generation of chemotherapeutic agent conjugates to ensure that the activity of the drug and/or protein does not diminish as a result of the conjugation process.

Examples of chemotherapeutic agents include the following non-mutually exclusive classes of chemotherapeutic agents: alkylating agents, anthracyclines, antibiotics, antifolates, antimetabolites, antitubulin agents, auristatins, chemotherapy sensitizers, DNA minor groove binders, DNA replication inhibitors, duocarmycins, etoposides, fluorinated pyrimidines, lexitropsins, nitrosoureas, platinols, purine antimetabolites, puromycins, radiation sensitizers, steroids, taxanes, topoisomerase inhibitors, and vinca alkaloids. Examples of individual chemotherapeutics that can be conjugated to a nucleic acid or protein of the invention include but are not limited to an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluorodeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thio TEPA, topotecan, vinblastine, vincristine, vinorelbine, VP-16 and VM-26.

The conjugates of the invention used for enhancing the therapeutic effect of the protein of the invention include non-classical therapeutic agents such as toxins. Such toxins include, for example, abrin, ricin A, pseudomonas exotoxin, or diphtheria toxin.

Techniques for conjugating such therapeutic moieties to proteins, and in particular to antibodies, are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc., 1985); Hellstrom et al., "Antibodies For Drug Delivery", in Controlled Drug Delivery (2nd ed.), Robinson et al. (eds.), pp. 623–53 (Marcel Dekker, Inc., 1987); Thorpe, "Antibody Carriers Of Cytotoxic Agents In Cancer Therapy: A Review", in Monoclonal Antibodies '84: Biological And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., 1982, Immunol. Rev. 62:119–58.

Alternatively, an antibody of the invention can be conjugated to a second antibody to form an antibody heteroconjugate as described by Segal in U.S. Pat. No. 4,676,980, which is incorporated herein by reference in its entirety.

As discussed above, in certain embodiments of the invention, a protein of the invention can be co-administered with a pro-drug converting enzyme. The pro-drug converting enzyme can be expressed as a fusion protein with or conjugated to a protein of the invention. Exemplary pro-drug converting enzymes are carboxypeptidase G2, beta-glucuronidase, penicillin-V-amidase, penicillin-G-amidase, β-lactamase, β-glucosidase, nitroreductase and carboxypeptidase A.

5.8 Gene Therapy

In a specific embodiment, nucleic acids of the invention are administered to treat, inhibit or prevent HD. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see, Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; Morgan and Anderson, 1993, Ann. Rev. Biochem. 62:191–217; May, 1993, TIBTECH 1, 1(5):155–215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the therapeutic comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, 1989, Proc. Natl. Acad. Sci. USA 86:8932–8935; Zijlstra et al., 1989, Nature 342: 435–438. In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, for example by constructing them as part of an appropriate nucleic acid expression vector and administering the vector so that the nucleic acid sequences become intracellular. Gene therapy vectors can be administered by infection using defective or attenuated retrovirals or other viral vectors (see, e.g., U.S. Pat. No. 4,980,286); direct injection of naked DNA; use of microparticle bombardment (e.g., a gene gun; Biolistic, Dupont); coating with lipids or cell-surface receptors or transfecting agents; encapsulation in liposomes, microparticles, or microcapsules; administration in linkage to a peptide which is known to enter the nucleus; administration in linkage to a ligand subject to receptor-mediated endocytosis (see, e.g., Wu and Wu, 1987, J. Biol. Chem. 262: 4429–4432) (which can be used to target cell types specifically expressing the receptors); etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06 180; WO 92/22635; WO92/20316; WO93/14188, and WO 93/20221). Alternatively, the nucleic acid can be introduced intracellularly and incorporated within host cell DNA for expression by homologous recombination (Koller and Smithies, 1989, Proc. Natl. Acad. Sci. USA 86:8932–8935; Zijlstra et al., 1989, Nature 342:435–438).

In a specific embodiment, viral vectors that contain nucleic acid sequences encoding an antibody of the invention are used. For example, a retroviral vector can be used (see Miller et al., 1993, Meth. Enzymol. 217:581–599). These retroviral vectors contain the components necessary for the correct packaging of the viral genome and integration into the host cell DNA The nucleic acid sequences encoding the antibody to be used in gene therapy are cloned into one or more vectors, thereby facilitating delivery of the gene into a patient. More detail about retroviral vectors can be found in Boesen et al., 1994, Biotherapy 6:29 1–302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Klein et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Another approach to gene therapy involves transferring a gene, e.g. an AC10 or HeFi-1 gene, to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to fibroblasts; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, 1992, Cell 71:973–985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of an protein or pharmaceutical composition include determining the effect of the protein or pharmaceutical composition on a Hodgkin's cell line or a tissue sample from a patient with Hodgkin's Disease. The cytotoxic and/or cytostatic effect of the protein or composition on the Hodgkin's cell line and/or tissue sample can be determined utilizing techniques known to those of skill in the art. A preferred method, described in Section 6 infra, entails contacting a culture of the Hodgkin's Disease cell line grown at a density of approximately of about 5,000 cells in a 0.33 cm$^2$ of culture area for a period of 72 hours with the protein or pharmaceutical composition, exposing the culture to 0.5 µCi of $^3$H-thymidine during the final 8 hours of said 72-hour period, and measuring the incorporation of $^3$H-thymidine into cells of the culture. The protein or pharmaceutical composition has a cytostatic or cytotoxic effect on the Hodgkin's Disease cell line and is useful for the treatment or prevention of Hodgkin's Disease if the cells of the culture have reduced $^3$H-thymidine incorporation compared to cells of the same Hodgkin's Disease cell line cultured under the same conditions but not contacted with the protein or pharmaceutical composition. Alternatively, in vitro assays which can be used to determine whether administration of a specific protein or pharmaceutical composition is indicated, include in vitro cell culture assays in which a tissue sample from a Hodgkin's Disease patient is grown in culture, and exposed to or otherwise a protein or pharmaceutical composition, and the effect of such compound upon the Hodgkin's tissue sample is observed.

5.9 Therapeutic/Prophylactic Administration and Compositions

The invention provides methods of treatment and prophylaxis by administration to a subject of an effective amount of a CD30-binding protein which has a cytotoxic or cytostatic effect on Hodgkin's Disease cells (i.e., a protein of the invention), a nucleic acid encoding said CD30-binding protein (i.e., a nucleic acid of the invention), or a pharmaceutical composition comprising a protein or nucleic acid of the invention (hereinafter, a pharmaceutical of the invention). According to the present invention, treatment of HD encompasses the treatment of patients already diagnosed as HD at any clinical stage; such treatment resulting in delaying tumor growth; and/or promoting tumor regression.

In a preferred embodiment, the protein of the invention is the monoclonal antibody AC10 or HeFi-1 or a fragment or derivative thereof. In a preferred aspect, a pharmaceutical of the invention comprises a substantially purified protein or nucleic acid of the invention (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed are described above; additional appropriate formulations and routes of administration can be selected from among those described herein below.

Various delivery systems are known and can be used to administer a nucleic acid or protein of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction include but are not limited to intradermal, intramuscular, intraperitoneal, intravenous, subcutaneous, intranasal, epidural, and oral routes. Nucleic acids and proteins of the invention may be administered by any convenient route, for example by infusion or bolus injection, by absorption through epithelial or mucocutaneous linings (e.g., oral mucosa, rectal and intestinal mucosa, etc.) and may be administered together with other biologically active agents such as chemotherapeutic agents (see Section). Administration can be systemic or local.

In a specific embodiment, it may be desirable to administer the nucleic acid or protein of the invention by injection, by means of a catheter, by means of a suppository, or by means of an implant, said implant being of a porous, non-porous, or gelatinous material, including a membrane, such as a sialastic membrane, or a fiber. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527–1533; Treat et al., 1989, in Liposomes in the Therapy of Infectious Disease and Cancer, Lopez-Berestein and Fidler (eds.), Liss, New York, pp. 353–365; Lopez-Berestein, ibid., pp. 317–327; see generally, ibid.)

In yet another embodiment, the compound or composition can be delivered in a controlled release system. In one embodiment, a pump may be used (see Langer, supra; Sefton, 1989, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105).

Other controlled release systems are discussed in the review by Langer, 1990, Science 249:1527–1533.

In a specific embodiment where a nucleic acid of the invention is administered, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

As alluded to above, the present invention also provides pharmaceutical compositions (pharmaceuticals of the invention). Such compostions comprise a therapeutically effective amount of a nucleic acid or protein of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the nucleic acid or protein of the invention, preferably in purified form, together with a suitable amount of carrier so as to provide the form for proper administration to the patient. The formulation should suit the mode of administration.

In a preferred embodiment, the pharmaceutical of the invention is formulated in accordance with routine procedures as a pharmaceutical composition adapted for intravenous administration to human beings. Typically, compositions for intravenous administration are solutions in sterile isotonic aqueous buffer. Where necessary, the pharmaceutical of the invention may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical of the invention is to be administered by infusion, it can be dispensed with an infusion bottle containing sterile pharmaceutical grade water or saline. Where the pharmaceutical of the invention is administered by injection, an ampoule of sterile water for injection or saline can be provided so that the ingredients may be mixed prior to administration.

The amount of the nucleic acid or protein of the invention which will be effective in the treatment or prevention of HD can be determined by standard clinical techniques. In addition, in vitro assays may optionally be employed to help identify optimal dosage ranges. The precise dose to be employed in the formulation will also depend on the route of administration, and the stage of HD, and should be decided according to the judgment of the practitioner and each patient's circumstances. Effective doses may be extrapolated from dose-response curves derived from in vitro or animal model test systems.

5.10 Kits

The invention also provides a pharmaceutical pack or kit comprising one or more containers filled with a nucleic acid or protein of the invention and optionally one or more pharmaceutical carriers. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a kit comprises a purified protein of the invention. In a preferred mode of the embodiment, the protein is an antibody. The protein may be conjugated to a radionuclide or chemotherapeutic agent. The kit optionally further comprises a pharmaceutical carrier.

In another embodiment, a kit of the invention comprises a nucleic acid of the invention, or a host cell comprising a nucleic acid of the invention, operably linked to a promoter for recombinant expression.

5.11 Effective Dose

Toxicity and therapeutic efficacy of the proteins of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Proteins that exhibit large therapeutic indices are preferred. While proteins that exhibit toxic side effects may be used, care should be taken to design a delivery system that targets such proteins to the site of affected tissue in order to minimize potential damage to uninfected cells and, thereby, reduce side effects.

The data obtained from the cell culture assays and animal studies can be used in formulating a range of dosage for use in humans. The dosage of such proteins lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

Generally, the dosage of a protein of the invention in a pharmaceutical of the invention administered to a Hodgkin's Disease patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign proteins. Thus, lower dosages of humanized, chimeric or human antibodies and less frequent administration is often possible.

5.12 Formulations

Pharmaceutical compositions for use in accordance with the present invention may be formulated in conventional manner using one or more physiologically acceptable carriers or excipients.

Thus, the proteins and their physiologically acceptable salts and solvates may be formulated for administration by inhalation or insufflation (either through the mouth or the nose) or oral, buccal, parenteral or rectal administration.

For oral administration, the pharmaceutical compositions may take the form of for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate) lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicles before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the proteins for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The proteins may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The proteins may also be formulated in rectal compositions such as suppositories or retention enemas, e.g., containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration preferably for administration to a human.

5.13 Combination Therapy for Treatment of Hodgkin's Disease

The nucleic acids and proteins of the invention can be administered together with treatment with irradiation or one or more chemotherapeutic agents.

For irradiation treatment, the irradiation can be gamma rays or X-rays. For a general overview of radiation therapy, see Hellman, Chapter 12: Principles of Radiation Therapy Cancer, in: Principles and Practice of Oncology, DeVita et al., eds., 2nd. Ed., J.B. Lippencott Company, Philadelphia.

Useful classes of chemotherapeutic agents include, but are not limited to, the following non-mutually exclusive classes of agents: alkylating agents, anthracyclines, antibiotics, antifolates, antimetabolites, antitubulin agents, auristatins, chemotherapy sensitizers, DNA minor groove binders, DNA replication inhibitors, duocarmycins, etoposides, fluorinated pyrimidines, lexitropsins, nitrosoureas, platinols, purine antimetabolites, puromycins, radiation sensitizers, steroids, taxanes, topoisomerase inhibitors, and vinca alkaloids. Individual chemotherapeutics encompassed by the invention include but are not limited to an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluorodeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In a specific embodiment, a nucleic acid or protein of the invention is administered concurrently with radiation therapy or one or more chemotherapeutic agents.

In another specific embodiment, chemotherapy or radiation therapy is administered prior or subsequent to administration of a nucleic acid or protein of the invention, by at least an hour and up to several months, for example at least an hour, five hours, 12 hours, a day, a week, a month, or three months, prior or subsequent to administration of a nucleic acid or protein of the invention.

In a specific embodiment in which a protein of the invention is conjugated to a pro-drug converting enzyme, or in which a nucleic acid of the invention encodes a fusion protein comprising a pro-drug converting enzyme, the protein or nucleic acid is administered with a pro-drug. Administration of the pro-drug can be concurrent with administration of the nucleic acid or protein of the invention, or, more preferably, follows the administration of the nucleic acid or protein of the invention by at least an hour to up to one week, for example about five hours, 12 hours, or a day. Depending on the pro-drug converting enzyme administered, the pro-drug can be a benzoic acid mustard, an aniline mustard, a phenol mustard, p-hydroxyaniline mustard-glucuronide, epirubicin-glucuronide, adriamycin-N phenoxyaceryl, N-(4'-hydroxyphenyl acetyl)-palytoxin doxorubicin, melphalan, nitrogen mustard-cephalosporin, α-phenylenediamine, vinblastine derivative-cephalosporin, cephalosporin mustard, cyanophenylmethyl-⊕-D-gluco-pyranosiduronic acid, 5-(adaridin-1-yl-)2,4-dinitrobenzamide, or methotrexate-alanine.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The invention is further described in the following examples which are in no way intended to limit the scope of the invention.

6. EXAMPLE:

Anti-CD30 Monoclonal Antibodies AC10 and HeFi-1 Inhibit the Growth of CD30 Expressing Hodgkin's Disease Cell Lines

6.1 Materials and Methods

Cells and culture conditions: The CD30 expressing cell lines, L540, HDLM2, L428, KM-H2 and Karpas 299, were obtained from the German Collection of Microorganisms and Cell Cultures/DSMZ in Braunschweig, Germany. The Hodgkin's cell line L540cy was a provided by Dr. V. Diehl of the University of Cologne, Cologne, Germany. The cell lines were maintained in the recommended media formulations and subcultured every 3–4 days.

Reagents and antibodies: Anti-CD30 monoclonal antibody hybridoma line AC10 was described by Bowen et al. (Bowen et al., 1993, J. Immunol. 151:5896–5906). Purified antibody was isolated from serum-free supernatants using a protein-G immunoaffinity column. The resulting AC10 antibody was determined to be >97% monomeric by size exclusion chromatography. The monoclonal antibody HeFi-1 has been previously described and was provided by Dr. T. Hecht, NCI, Bethesda, Md. HeFi-1 mAb was demonstrated by size exclusion chromatography to be greater than 98% monomer.

Proliferation assays: CD30 expressing cell lines were cultured in flat-bottom 96-well plates at a density of 50,000 or 5,000 cells/well in growth media (RPMI with 10% fetal bovine serum (FBS) for cell lines L428, KM-H2 and Karpas 299, and RPMI/20% FBS for cell lines HDLM-2 and L540. The cell lines were cultured in the absence or presence of cross-linked soluble anti-CD30 mAbs or immobilized anti-CD30 mAbs, as described below.

Antibody cross-linking in solution: To cross-link the anti-CD30 antibodies in solution, various dilutions of AC10 or HeFi-1 were titrated into 96-well flat bottom tissue culture plates in the absence or presence of 20 μg/ml polyclonal goat anti-mouse IgG antibodies. Hodgkin's disease cell lines were then added to the plates at either 50,000 or 5,000 cells/well. The plates were incubated at 37° C. for 72 hours and were labeled with $^3$H-thymidine, 1 μCi/well, for the final 5 hours.

Antibody immobilization: Antibody immobilization was obtained by coating wells with antibody in 50 mmol/L Tris buffer (pH 8.5) for 18 hours at 4° C. Prior to the addition of cells, wells were washed twice with PBS to remove unbound mAb. 50,000 or 5,000 cells in a total volume of 200 μl were added to each well. Proliferation was determined by uptake of $^3$H-thymidine (0.5 μCi/well) during the final 8 hours of a 72 hour culture period.

6.2 Results

To evaluate the biologic activity of anti-CD30 mAbs, CD30-expressing HD cell lines (50,000 cells/well) were cultured in the presence of immobilized anti-CD30 mAb AC10. mAb AC10 demonstrated inhibition of cell growth of T-cell-like (L540 and HDLM-2) or B-cell-like (L428 and KM-H2) HD lines (FIG. 1). Ki-1, which was previously shown to have no effect on HD cell lines (Gruss et al., 1996, Blood 83:2045–2056), was used as a control.

To further evaluate the activity of AC10, a second series of assays were performed. In order to assess the activity of the AC10 during a period of logarithmic tumor cell growth, the cell density of the cultures was decreased to provide more optimal growth conditions. To that end, HD cell lines were cultured in flat-bottom 96 well plates at a density of 5,000 cells/well in the presence or absence of mAb AC10. AC10 demonstrated growth inhibition of all four HD cell lines tested (L540, HDLM-2, L428 and KM-H2; FIG. 2).

In another set of experiments, HD cell lines were incubated with soluble AC10 or HeFi-1 that were cross-linked in solution by the addition of soluble goat anti-mouse IgG antibodies. Under these cross-linking conditions, all four HD cell lines, when plated at $5 \times 10^4$ cell/well, were growth inhibited by AC10 and HeFi-1 (FIG. 3). When the cells were plated at $5 \times 10^3$ cell/well, all four HD cell lines were growth inhibited by AC10, while three of the four cell lines, HDLM-2, L540, and L428, were growth inhibited by HeFi-1 (FIG. 4).

The data resulting from the experiments testing the effects of AC10 and HeFi-1 on CD30-expressing tumor cell lines are summarized in Table 2, infra. Table 2 further provides a comparison of the anti-tumor activity of AC10 and HeFi-1 with that of mAb M44.

TABLE 2

Cytostatic and/or cytotoxic activity of signaling anti-CD30 mAbs on CD30-expressing malignant cell lines

| | | Inhibition of Growth by | | |
|---|---|---|---|---|
| Cell Line | Cell Type | M44[a] | HeFi-1 | AC10 |
| Karpas 299 | ALCL | + | + | + |
| Michel | ALCL | + | ND | ND |
| KM-H2 | HD (B cell phenotype) | − | + | + |
| L428 | HD (B cell phenotype) | − | + | + |
| HDLM-2 | HD (T cell phenotype) | − | + | + |
| L540 | HD (T cell phenotype) | − | + | + |

[a]Published data from Gruss et al, Blood 83(8): 2045–2056

Taken together, these data indicate that mAbs AC10 and HeFi-1 are distinguished from the previously described anti-CD30 mAbs by their ability to inhibit the growth of CD30-expressing HD lines. It is of interest to note that Hubinger et al. recently evaluated the activity of the anti-CD30 mAb M44, in immobilized form, in a proliferation assay utilizing 5,000 cells/well. Under these conditions, M44 inhibited the growth of the CD30-expressing ALCL line, Karpas 299 but not the HD cell line HDLM-2 (Hubinger et al., 1999, Exp. Hematol. 27(12):1796–805).

7. AC10 Enhances the Cytotoxic Effect of Chemotherapeutics on Hodgkin's Disease Cell Lines

7.1 Materials and Methods

L428 cells were cultured for 24 hours in the presence or absence of 0.1 μg/ml anti-CD30 antibody, AC10, crosslinked by the addition of 20 μg/ml goat anti-mouse IgG antibodies. After the 24-hour culture period, the cells were harvested and washed with phosphate buffered saline (PBS). The cells were then plated into 96-well flat-bottom tissue culture plates at $5 \times 10^3$ cells/well and mixed with various dilutions of chemotherapeutic drugs. After a 1-hour exposure to the drugs the cells were washed twice, followed by the addition of fresh culture media. The plates were then incubated at 37° C. for 72 hours followed by a 4-hour incubation with 0.5 μCi/well $^3$H-thymidine. The inhibition of growth was determined by comparing the amount of $^3$H-thymidine incorporated into treated cells to the amount incorporated into untreated control cells.

7.2 Results

To evaluate the effect of the anti-CD30 mAb in combination with chemotherapeutic drugs, L428 cells were incubated for 24 hours in either the absence of antibody or the presence of AC10 at 0.1 µg/ml with 20 µg/ml goat anti-mouse IgG to provide crosslinking for the primary antibody. After this incubation the cells were plated into 96-well tissue culture plates at 5×10$^3$ cells/well in the presence of dilutions of chemotherapeutic drugs including doxorubicin, cisplatin, and etoposide (Table 3). The EC$_{50}$, concentration of drug needed to inhibit the incorporation of $^3$H-thymidine by 50% compared to untreated control cells, was then determined for cells treated with the drugs alone or the combinations of drug and antibody. For doxorubicin, incubation with AC 10 decreased the EC$_{50}$ on L428 cells (i.e. decreased the amount of drug necessary to inhibit 50% of DNA synthesis) from approximately 45 nM (doxorubicin alone) to approximately 9 nM, for cisplatin AC10 decreased the EC$_{50}$ from ~1,500 nM to ~500 nM, and for etoposide AC10 decreased the EC$_{50}$ from ~1,500 nM to ~600 nM.

TABLE 3

AC10 enhances the effectiveness of chemotherapeutic drugs on the HD cell line L428.

| Drug | EC$_{50}$, nM | |
|---|---|---|
| | with AC10 | without AC10 |
| Doxorubicin | 45 | 9 |
| Cisplatin | 1,500 | 500 |
| Etoposide | 1,500 | 600 |

8. Antitumor Activity of AC10 and HeFi-1 in Disseminated and Localized (Subcutaneous) L540CY Hodgkin's Disease Xenografts

8.1 Materials and Methods

Human tumor xenograft models: Female C.B-17 SCID mice, obtained from Taconic (Germantown, N.Y.) at 4–6 weeks of age, were used for all efficacy studies. To establish xenograft models of Hodgkin's disease, L540cy (HD) cells were harvested from cell culture, washed in ice cold phosphate buffered saline (PBS), resuspended in PBS, and maintained on ice until implantation. For disseminated disease models, mice were injected intravenously through the tail vein with 10$^7$ L540cy cells. Solid tumor xenografts were established by injecting mice subcutaneously (s.c.) with 2×10$^7$ L540cy cells. For therapeutic evaluation the indicated treatment doses and schedules were used.

Administration of AC10 and HeFi-1: Disseminated L540cy tumor bearing mice received 10$^7$ cells through the tail vein on d0 followed by therapy initiated on d1. Treated mice received i.p. injections of either AC10 or HeFi-1 every two days for a total of 10 injections, q2d×10, at 1 mg/kg/injection.

For the subcutaneous L540cy model, mice were injected s.c. with 2×10$^7$ cells and were observed daily for solid tumor formation. When tumors were palpable, the animals were randomly distributed into groups and received either AC10 or HeFi-1 q2d×10 at 2 mg/kg/injection.

8.2 Results

Figure 5A:
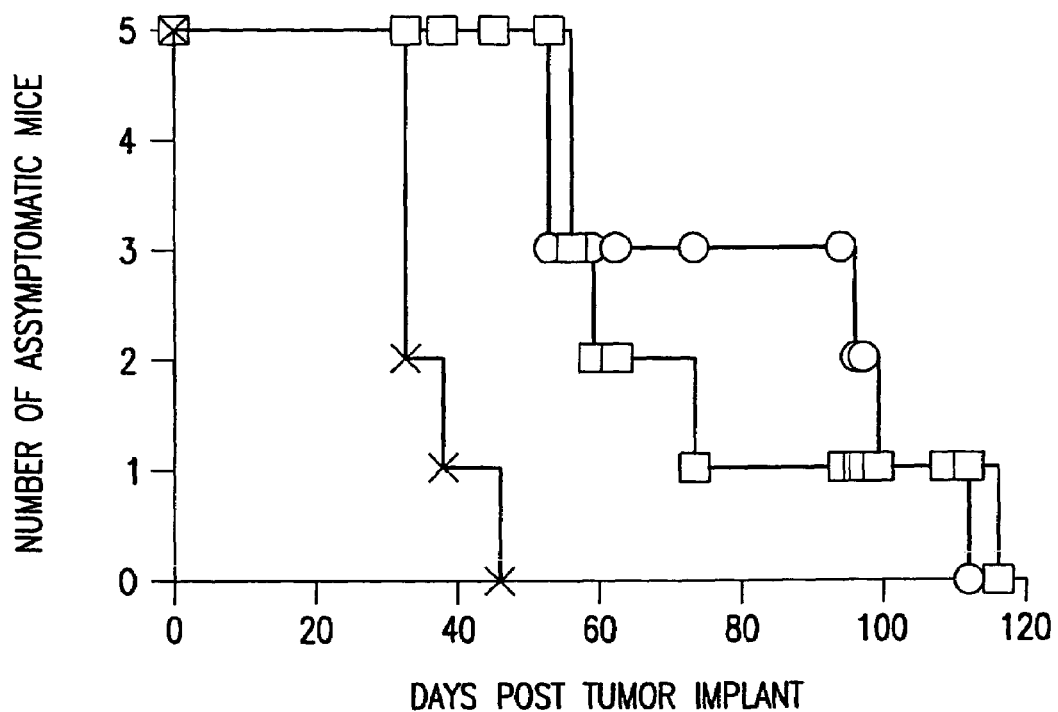

AC10 and HeFi-1 were tested in L540cy Hodgkin's disease xenografted SCID mice, as described above. In the mouse population with disseminated L540cy tumors, all of the untreated control animals developed signs of severe disseminated disease such as hind limb paralysis or the formation of a solid tumor mass and had to be sacrificed (mean survival time=37 days). In contrast, all of the mice that received either AC10 or HeFi-1 survived for >46 days with no signs of disease (FIG. 5A).

Figure 5B:
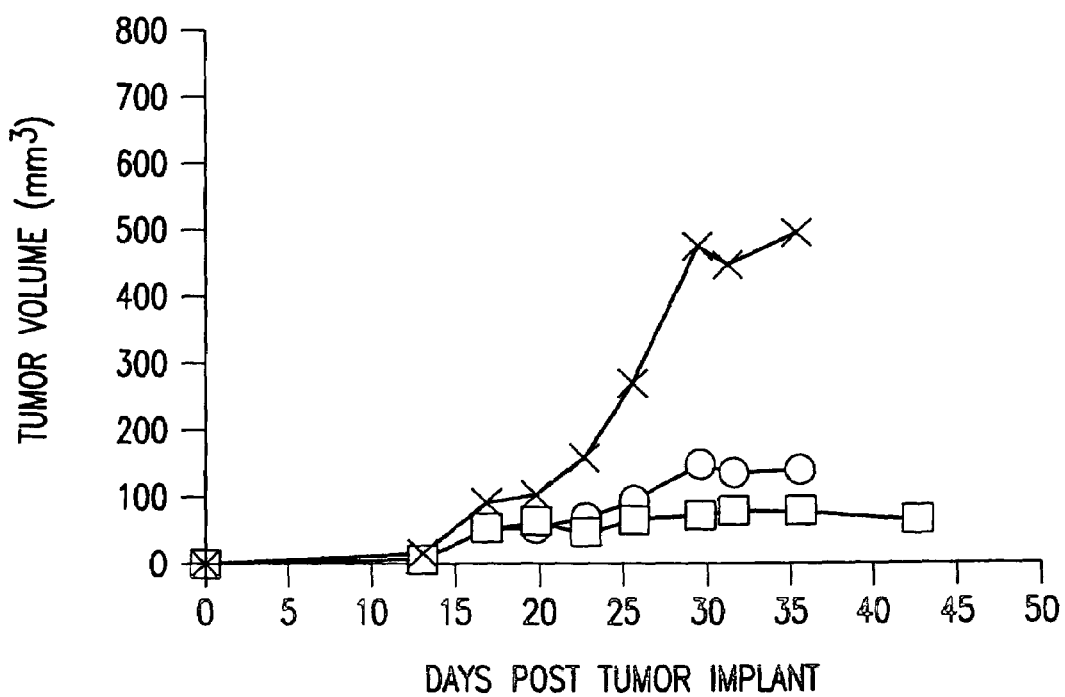

With respect to the mouse population with subcutaneous L540cy tumors, while the untreated control tumors rapidly grew to >450 mm$^3$, both mAbs significantly delayed tumor growth as shown in FIG. 5B.

The inventors have identified murine monoclonal antibodies (mAbs) which target the human CD30 receptor and display a profile of activity not previously described for other anti-CD30 mAbs. In unmodified form, these antibodies, AC10 and HeFi-1 inhibit the growth of HD and the ALCL Line Karpas 299 and display in vivo antitumor activity in a tumor xenograft model of Hodgkin's disease.

9. Antitumor Activity of Chimeric AC10 in Subcutaneous L540CY Hodgkin's Disease Xenografts

9.1 Materials and Methods

Chimeric AC10 (cAC 10) was generated via homologous recombination essentially as previously described using human IgG1-kappa heavy and light chain conversion vectors (Yarnold and Fell, 1994, Cancer Res. 54: 506–512). These vectors were designed such that the murine immunoglobulin heavy and light chain constant region loci are excised and replaced by the human gamma 1 and kappa constant region loci via homologous recombination. The resulting chimeric hybridoma cell line expresses a chimeric antibody consisting of the heavy and light chain variable regions of the original monoclonal antibody and the human gamma 1 and kappa constant regions.

9.2 Results

To evaluate the efficacy of cAC10 in vivo, SCID mice were implanted subcutaneously with L540cy cells as described above. When the tumors reached an average size of greater than 150 mm$^3$ the mice were divided into groups that were either untreated or treated with 2 mg/kg cAC 10 twice per week for a total of five injections. The tumors in the untreated mice rapidly grew to an average size of greater than 600 mm$^3$ (FIG. 6). In contrast, the average tumor size in the animals treated with cAC 10 remained about the same size.

10. SPECIFIC EMBODIMENTS CITATION OF REFERENCES

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various references, including patent applications, patents, and scientific publications, are cited herein, the disclosures of which are incorporated herein by reference in their entireties.

What is claimed is:

1. A method for the treatment of Hodgkin's Disease in a subject comprising administering to the subject, in an amount effective for said treatment, (a) an antibody that (i) immunospecifically binds CD30 and (ii) exerts a cytostatic or cytotoxic effect on a Hodgkin's Disease cell line, wherein said antibody exerts the cytostatic or cytotoxic effect on the Hodgkin's Disease cell line in the absence of conjugation to a cytostatic or cytotoxic agent and in the absence of cells other than cells of said Hodgkin's Disease cell line; and (b) a pharmaceutically acceptable carrier.

2. The method of claim 1, wherein the antibody is human, humanized or chimeric.

3. The method of claim 1, further comprising administering chemotherapy to said subject.

4. The method of claim 1, wherein the antibody is conjugated to a cytotoxic agent.

5. The method of claim 1, wherein the antibody is a fusion protein comprising an antigen binding region that immunospecifically binds to CD30 and an amino acid sequence of a second protein that is not an antibody.

6. The method of claim 4 or 5, further comprising administering chemotherapy to said subject.

7. The method of claim 1, wherein the cytostatic or cytotoxic effect of the antibody is exhibited upon performing a method comprising:
   (a) contacting a culture of the Hodgkin's Disease cell line with the antibody, said culture being of about 5,000 cells in a culture area of about 0.33 cm$^2$, said contacting being for a period of 72 hours;
   (b) exposing the culture to 0.5 µCi of $^3$H-thymidine during the final 8 hours of said 72 hour period; and
   (c) measuring the incorporation of the $^3$H-thymidine into cells of the culture,
   wherein the antibody has a cytostatic or cytotoxic effect on the Hodgkin's Disease cell line if the cells of the culture have reduced $^3$H-thymidine incorporation compared to cells of the same Hodgkin's Disease cell line cultured under the same conditions but not contacted with the antibody.

8. A method for the treatment of Hodgkin's Disease in a subject comprising administering to the subject an amount of an antibody, which antibody (a) competes for binding to CD30 with monoclonal antibody AC10 or HeFi-1, and (b) exerts a cytostatic or cytotoxic effect on a Hodgkin's Disease cell line in the absence of cell other than cells of said Hodgkin's Disease cell line, which amount is effective for the treatment of Hodgkin's Disease.

9. A method for the treatment of Hodgkin's Disease in a subject comprising administering to the subject an amount of an antibody, which antibody (a) comprises the amino acid sequence that has at last 95% identity to SEQ ID NO:2, (b) immunospecifically binds CD30, and (c) exerts a cytostatic or cytotoxic effect on a Hodgkin's Disease cell line in the absence of cells other than cells of said Hodgkin's Disease cell line which amount is effective for the treatment of Hodgkin's Disease.

10. The method of any one of claims 8 or 9, wherein the antibody is a human, humanized or chimeric antibody.

11. The method of any one of claims 8 or 9, wherein comprising administering chemotherapy to said subject.

12. The method of any one of claims 8 or 9, wherein the antibody is conjugated to a cytotoxic agent.

13. The method of any one of claims 8 or 9, wherein the antibody is fusion protein comprising an antigen binding region that immunospecifically binds to CD30 and the amino acid sequence of a second protein.

14. The method of claim 13, further comprising administering chemotherapy to the subject.

15. The method of claim 14, further comprising administering chemotherapy to the subject.

16. The method of any one of claims 8 or 9, wherein the cytostatic or cytotoxic effect is exhibited upon performing a method comprising:
   (a) contacting a culture of the Hodgkin's Disease cell line with the antibody, said culture being of about 5,000 cells in a culture area of about 0.33 cm$^2$, said contacting being for a period of 72 hours;
   (b) exposing the culture to 0.5 µCi of $^3$H-thymidine during the final 8 hours of said 72 hour 72 our period; and
   (c) measuring the incorporation of the $^3$H-thymidine into cells of the culture, wherein the antibody has a cytostatic or cytotoxic effect on the Hodgkin's Disease cell line if the cells of the culture have reduced $^3$H-thymidine incorporation compared to cells of the same Hodgkin's Disease cell line cultured under the same conditions but not contacted with the antibody.

17. A method for the treatment of Hodgkin's Disease in a subject comparing administering to the subject, in an amount effective for said treatment, (a) an antibody that (i) immunospecifically binds CD30 and (ii) exerts a cytostatic or cytotoxic effect on a Hodgkin's Disease cell line, wherein the antibody exerts the cytostatic or cytotoxic effect on the Hodgkin's Disease cell line in the absence of conjugation to a cytostatic or cytotoxic agent and (b) a pharmaceutically acceptable carrier,
   wherein the cytostatic or cytotoxic effect of the antibody is exhibited upon performing a method comprising:
   (A) immobilizing said antibody in a well, said well having a culture area of about 0.33 cm$^2$;
   (B) adding about 5,000 cells of the Hodgkin's Disease cell line in the presence of RPMI with 20% fetal bovine serum to the well:
   (C) culturing the cells in the presence of said antibody and RPMI with 20% fetal bovine scrum for a period of 72 hours to form a Hodgkin's Disease cell culture;
   (D) exposing the Hodgkin's Disease cell culture to 0.5 µCi/well of $^3$H-thymidine during the final 8 hours of said 72 hour period; and
   (E) measuring the incorporation of the $^3$H-thymidine into cells of the Hodgkin's Disease cell culture,
   wherein the antibody has a cytostatic or cytotoxic effect on the Hodgkin's Disease cell line if the cells of the Hodgkin's Disease cell culture have reduced $^3$H-thymidine incorporation compared to cells of the same Hodgkin's Disease cell line cultured under the same conditions but not contacted with the antibody.

18. A method for the treatment of Hodgkin's Disease in a subject comprising administering to the subject, in an amount effective for said treatment, (a) a chimeric, humanized or human antibody that (i) immunospecifically binds CD30 and (ii) exerts a cytostatic or cytotoxic effect on a Hodgkin's Disease cell line, wherein the chimeric, humanized or human antibody exerts the cytostatic or cytotoxic effect on Hodgkin's Disease cell line in the absence of conjugation to a cytostatic or cytotoxic agent and (b) a pharmaceutically acceptable carrier,
   wherein the cytostatic or cytotoxic effect of the chimeric, humanized or antibody is exhibited upon performing a method comprising:
   (A) contacting a culture of the Hodgkin's Disease cell line with the chimeric, humanized or human antibody, said culture being of about 5,000 cells in a culture area of about 0.33 cm$^2$, said contacting being for a period of 72 hours;
   (B) adding a cross-linking antibody to the Hodgkin's Disease cell line, the cross-linking antibody binding to the chimeric, humanized or human antibody;
   (C) exposing the culture to 0.5 µCi of $^3$H-thymidine during the final 8 hours of said 72-hour period; and
   (D) measuring the incorporation of the $^3$H-thymidine into cells of the culture, wherein the chimeric, humanized or human antibody has a cytostatic or cytotoxic effect on the Hodgkin's Disease cell line if the cells of the culture have reduced $^3$H-thymidine incorporation compared to cells of the same Hodgkin's Disease cell line cultured under the same conditions but not contacted with the chimeric, humanized or human antibody.

* * * * *